United States Patent [19]

Kinoshita et al.

[11] Patent Number: 5,112,867
[45] Date of Patent: May 12, 1992

[54] TRIPHENYLMETHANE DERIVATIVES

[75] Inventors: Iwao Kinoshita; Daisuke Machii; Yasuo Onoda; Haruki Takai; Nobuo Kasaka, all of Shizuoka; Katsuichi Shuto, Mishima; Katsushige Gomi, Shizuoka; Makoto Morimoto, Machida; Akio Ishii, Shizuoka, all of Japan

[73] Assignee: Kyowa Hakko Gogyo Co., Ltd., Tokyo, Japan

[21] Appl. No.: 515,873

[22] Filed: Apr. 27, 1990

[30] Foreign Application Priority Data

Apr. 28, 1989 [JP] Japan .................. 1-110995

[51] Int. Cl.$^5$ .................. A61K 31/165; C07C 103/22
[52] U.S. Cl. .................. 514/617; 514/237.8; 514/546; 514/547; 514/548; 514/622; 544/155; 544/166; 544/60; 544/360; 544/394; 540/479; 546/191; 546/194; 546/234; 560/140
[58] Field of Search .................. 560/140; 564/171, 174; 514/546-548, 622, 237.8; 544/166

[56] References Cited

U.S. PATENT DOCUMENTS 4,304,833  12/1981  Foley .................. 430/221

OTHER PUBLICATIONS

Foley, "Chemical Abstracts", vol. 96, 1982, col. 96:53845t.

Bindal et al., "Chemical Abstracts," vol. 113, 1990, Col. 113:90516v.
Chemical Abstracts 53, 21801f (1959).
Chemical Abstracts 64, 19789g (1966).
Chemical Abstracts 55, 19926 (1961).
Arch. Pharm., 292, 690 (1959).
Arch. Pharm. 293, 733 (1960).
J. C. S. Perkin I., 1211 (1978).
Yakugaku Zasshi, 81, 521 (1961).

Primary Examiner—C. Warren Ivy
Assistant Examiner—James H. Turnipseed
Attorney, Agent, or Firm—Fitzpatrick, Cella, Harper & Scinto

[57] ABSTRACT

A triphenylmethane derivative represented by the following general formula:

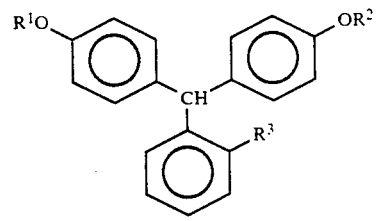

exhibits born absorption inhibiting effects and is useful as a medicament for treating osteoporosis.

8 Claims, No Drawings

TRIPHENYLMETHANE DERIVATIVES

BACKGROUND OF THE INVENTION

The present invention relates to a novel triphenylmethane derivative which is useful as a medicament for treating osteoporosis.

Hitherto, phenolphthalin derivatives in which a carboxyl group is subjected to amidation are known. Chem. Abst., 53, 21801f (1959) discloses phenolphthalin derivatives in which carboxyl is modified to amide. Chem. Abst., 64, 19789g (1966) discloses those in which carboxyl is modified to anilide. Japanese Published Unexamined Patent Application No. 132,336/81 discloses phenolphthalin derivatives in which carboxyl is modified to methylamide.

J.C.S. Perkin I., 1978, 1211 and Archiv der Pharmazie 292, 690 (1952) describe phenolphthalin derivatives in which carboxyl is changed to amino.

In Arch. Pharm., 293, 733 (1960) are disclosed phenolphthalin derivatives represented by the following structural formula (P):

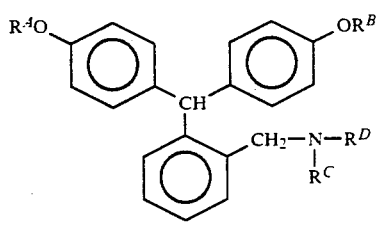

in which $R^A$, $R^B$ and $R^D$ are hydrogen, and $R^C$ is hydrogen, n-butyl or thioanilide; and phenolphthalin derivatives represented by the above formula in which $R^C$ is hydrogen, and $R^A$, $R^B$ and $R^D$ represent acetyl. In Arch. Pharm., 292, 690 (1959) are disclosed phenolphthalin derivatives represented by the formula (P) in which both of $R^A$ and $R^B$ are hydrogen, and both of $R^C$ and $R^D$ are methyl or ethyl, or $R^C$ and $R^D$ are combined with nitrogen atom adjacent thereto together to form

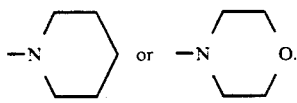

It has however been not known that triphenylmethane derivatives are useful as a medicament for treating osteoporosis.

SUMMARY OF THE INVENTION

The present invention provides triphenylmethane derivatives represented by the following formula (I):

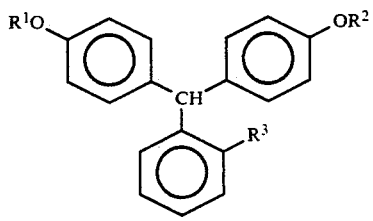

wherein each of $R^1$ and $R^2$ independently represents hydrogen, lower alkyl, aralkyl, lower alkanoyl or lower alkoxymethyl; $R^3$ represents —$CONR^4R^5$ where each of $R^4$ and $R^5$ independently represents hydrogen, unsubstituted or substituted lower alkyl, cycloalkyl, allyl, unsubstituted or substituted aralkyl, styryl, or unsubstituted or substituted aryl,

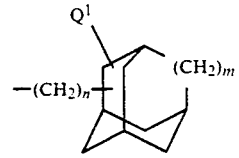

where $Q^1$ represents hydrogen or lower alkyl, m is an integer of 0 or 1, and n is an integer of 0–5,

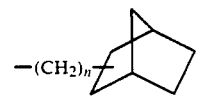

where n has the same meaning as previously defined,

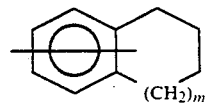

where m has the same meaning as previously defined,

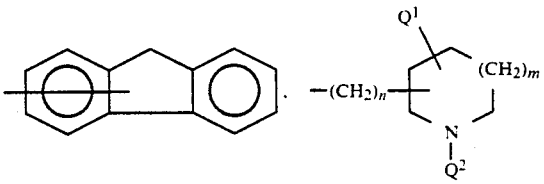

where $Q^2$ represents hydrogen, lower alkyl, or unsubstituted or substituted aralkyl, $Q^1$, m and n have the same meaning as previously defined,

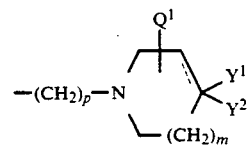

where ⋯⋯is single bond or double bond, $Y^1$ is hydrogen, $Y^2$ represents hydrogen, lower alkyl, unsubstituted or substituted aryl, pyridyl, piperidino or

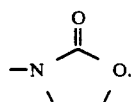

or $Y^1$ and $Y^2$ are combined together to form oxygen or —$(CH_2)_5$—, p is an integer of 1–5, and $Q^1$ and m have the same meaning as previously defined.

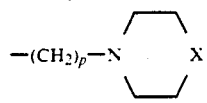

where X represents oxygen, sulfur or

where $Q^3$ represents hydrogen, lower alkyl, unsubstituted or substituted aralkyl, unsubstituted or substituted aryl, pyridyl or lower alkoxycarbonyl, and p has the same meaning as previously defined,

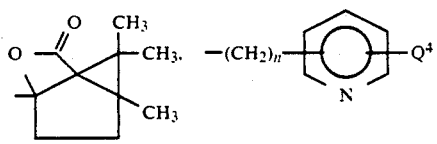

where $Q^4$ represents hydrogen, unsubstituted or substituted aryloxy, or halogen-substituted or unsubstituted pyridyloxy, and n has the same meaning as previously defined,

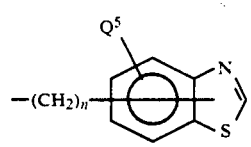

where $Q^5$ represents hydrogen, lower alkyl, lower alkoxyl or aryl, and n has the same meaning as previously defined,

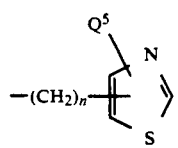

where $Q^5$ and n have the same meanings as previously defined,

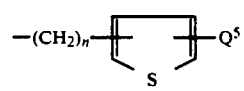

where $Q^5$ and n have the same meanings as previously defined, or

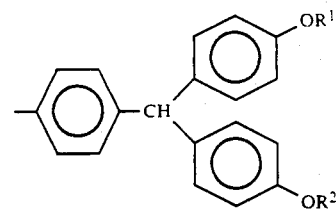

where $R^1$ and $R^2$ have the same meanings as previously defined (hereinafter, the foregoing definitions for $R^4$ and $R^5$ are referred to as "Group A"); or $R^4$ and $R^5$ are combined with nitrogen atom adjacent thereto to form a heterocyclic ring selected from the group consisting of

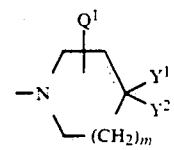

where $Q^1$, $Y^1$, $Y^2$ and m have the same meanings as previously defined,

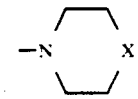

where X has the same meaning as previously defined,

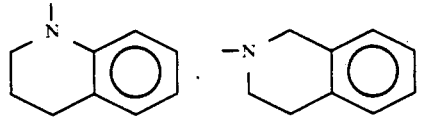

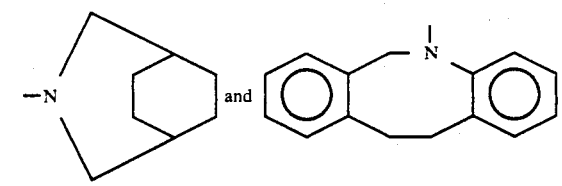

(hereinafter the foregoing heterocyclic rings are referred to as "Group B"), provided that when $R^4$ is hydrogen, $R^5$ represents the other groups than hydrogen, methyl and phenyl,

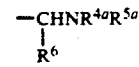

where $R^6$ represents hydrogen or lower alkyl, and each of $R^{4a}$ and $R^{5a}$ independently represents Group A or Group B, provided that when $R^{4a}$ is hydrogen, $R^{5a}$ represents the other groups than hydrogen and butyl, or both of $R^{4a}$ and $R^{5a}$ represent the other groups than methyl and ethyl, or $R^{4a}$ and $R^{5a}$ are combined with nitrogen atom adjacent thereto to form the other groups denoted by Group B than piperidino and morpholino, or

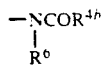

where $R^{4h}$ is Group A. and $R^6$ has the same meaning as previously defined; or a pharmaceutically acceptable salt thereof.

DETAILED DESCRIPTION OF THE INVENTION

In the definitions of the respective groups in the general formula (I), the lower alkyl and the alkyl moiety in the lower alkoxy, lower alkoxymethyl and lower alkoxycarbonyl means a straight or branched alkyl having 1 to 6 carbon atoms, for example, methyl, ethyl, propyl, isopropyl, butyl, isobutyl, sec-butyl, tert-butyl, pentyl, neopentyl, hexyl, etc. The cycloalkyl means cycloalkyls having 3 to 8 carbon atoms, for example, cyclopropyl, cyclopentyl, cyclohexyl, cyclooctyl, etc. The lower alkanoyl means a straight or branched alkanoyls having 1 to 5 carbon atoms, such as formyl, acetyl, propionyl, butyryl, isobutyryl, valeryl, pivaloyl, etc. The aralkyl means benzyl, benzhydryl, trityl, phenethyl, 1,2-diphenylethyl, etc. The aryl and aryl moiety in aryloxy mean phenyl, naphthyl, etc.

The number of the substituents for substituted alkyl is one to 3. The substituents are same or different, and include, for example, lower alkoxyl, mono- or di-alkyl-substituted amino or halogen.

The number of substituents for aryl and the aromatic moiety in the aralkyl is one to 3. The substituents are same or different, and include, for example, lower alkyl, trifluoromethyl, hydroxyl, lower alkoxyl, lower alkylthio, halogen, nitro, amino, lower alkanoyl, aroyl, morpholino, carboxyl, lower alkoxycarbonyl, etc. The lower alkyl and alkyl moiety in lower alkylthio and lower alkoxycarbonyl mean the same significance as defined for alkyl. The lower alkanoyl and aryl moiety in aroyl has the same meaning as previously defined. Halogen means fluorine, chlorine, bromine or iodine.

As the pharmaceutically acceptable salts of Compound (I), mention may be made of the acid addition salt such as hydrochloride, hydrobromide, hydroiodide, nitrate, sulfate, phosphate, formate, acetate, benzoate, maleate, fumarate, succinate, tartarate, citrate, oxalate, glyoxylate, asparate, methanesulfonate, ethanesulfonate, benzenesulfonate, and the like.

Processes for producing Compound (I) are described below.

Compound (Ia), which is Compound (I) in which $R^1$ and $R^2$ are other groups than hydrogen and $R^3$ is —CONR$^4$R$^5$ can be prepared from phenolphthalin represented by the formula (II) in accordance with the following reaction steps:

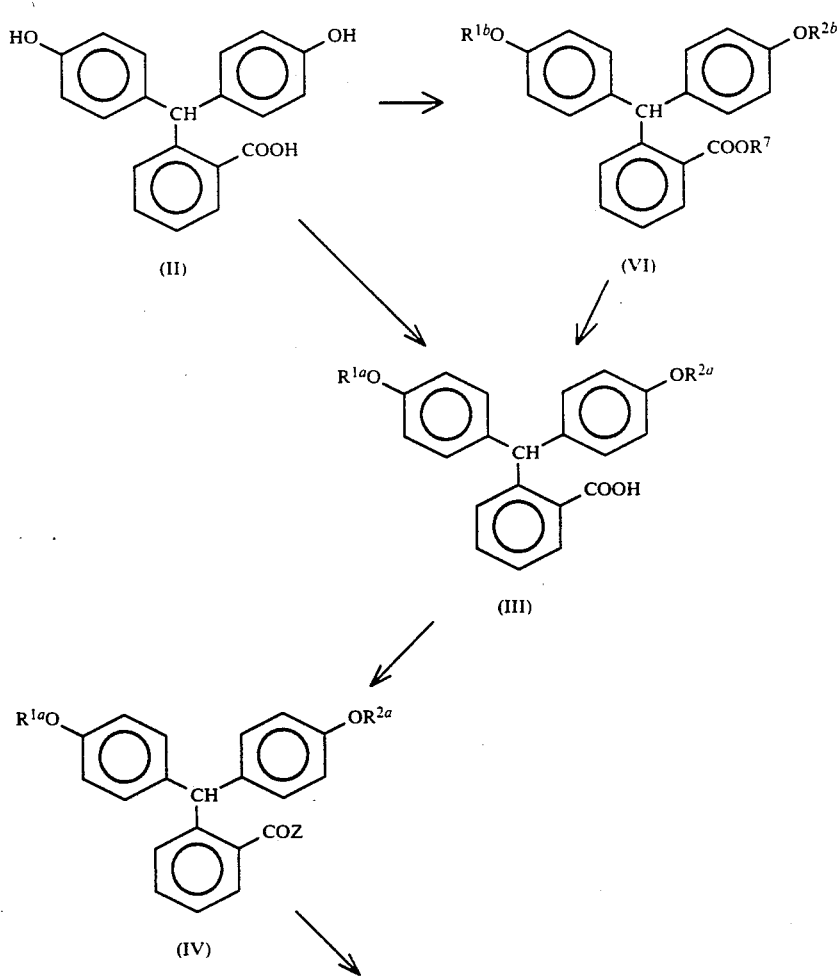

-continued

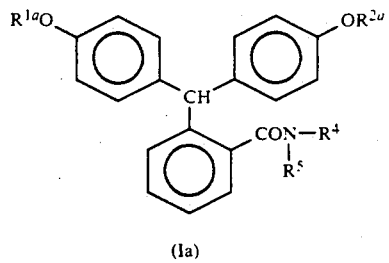

(Ia)

wherein $R^{1a}$ represents other groups denoted by $R^1$ than hydrogen, $R^{2a}$ represents other groups denoted by $R^2$ than hydrogen, $R^{1b}$ represents other groups denoted by $R^1$ than hydrogen and lower alkanoyl, $R^{2b}$ represents other groups denoted by $R^2$ than hydrogen and alkanoyl, $R^7$ has the same meanings as defined for $R^{1b}$ and $R^{2b}$; Z represents halogen, such as chlorine, bromine and iodine; and $R^4$ and $R^5$ have the same meanings as previously defined.

Compounds (VI), in which $R^{1b}$ and $R^{2b}$ are lower alkyl or aralkyl is prepared by reacting Compound (II) with an alkylating agent or an aralkylating agent. As the alkylating agent, mention may be made of halogenated alkyls, such as methyl iodide, ethyl iodide, propyl iodide, isopropyl iodide, methyl bromide, ethyl bromide, propyl bromide and isopropyl bromide; dialkylsulfuric acids, such as dimethylsulfuric acid; and diazoalkanes, such as diazomethane. As the aralkylating agent, mention may be made of halogenated aralkyls, such as benzyl bromide and benzyl chloride. In the alkylation and aralkylation reactions, any solvent can be used as the reaction solvent, so long as it does not interfere with the reaction. As the solvent, mention may be made of halogenated hydrocarbons, such as dichloromethane, chloroform, dichloroethane and carbon tetrachloride; aromatic hydrocarbons such as benzene, toluene and xylene; ketones such as acetone and methyl ethyl ketone; alcohols such as methanol, ethanol and isopropanol; ethers such as diethyl ether, dioxane and tetrahydrofuran; amides such as formamide and dimethylformamide; acetonitrile; ethyl acetate; dimethyl sulfoxide and the like. The solvent can be used either alone or in combination. Usually, the reaction proceeds at a temperature of from 0° C. to the boiling point of the solvent used and terminates in 1 to 72 hours. If desired, the reaction may be carried out in the presence of an inorganic base, such as sodium hydroxide, potassium hydroxide, sodium carbonate, potassium carbonate, cesium carbonate, sodium hydrogencarbonate and silver oxide, or an organic base such as triethylamine, N,N-diisopropylethylamine, N-methylmorpholine, pyridine and dimethylaminopyridine, so as to allow the reaction to proceed smoothly.

Compound (VI) in which $R^{1b}$ and $R^{2b}$ are lower alkoxymethyl is prepared by reacting Compound (II) with an alkoxymethylating agent. As the alkoxymethylating agents, mention may be made of methoxymethyl chloride, 2-methoxyethoxymethyl chloride and the like. The reaction is carried out in a similar manner as in the alkylation reaction described above.

Compound (III) in which $R^{1a}$ and $R^{2a}$ are lower alkyl, aralkyl or lower alkoxymethyl is prepared by hydrolyzing Compound (VI) with an acid or an alkali. As the acid, mention may be made of mineral acids such as hydrochloric acid and sulfuric acid; and organic acids such as formic acid, acetic acid and trifluoroacetic acid. As the alkali, mention may be made of sodium hydroxide, potassium hydroxide and the like. As the reaction solvent, water is used in addition to those mentioned hereinabove. Usually, the reaction proceeds at a temperature of from 0° C. to the boiling point of the reaction solvent used and terminates in 1 to 24 hours.

Compound (III) in which $R^{1a}$ and $R^{2a}$ are lower alkanoyl is prepared by reacting Compound (II) with an acylating agent. As the acylating agent, mention may be made of the reactive derivative of corresponding carboxylic acids, for example, acid anhydrides such as acetic anhydride and propionic anhydride; and acid halides such as acetyl chloride and acetyl bromide. The acylation reaction is carried out in a similar manner as in the alkylation reaction described hereinabove.

Compound (IV) is prepared by reacting Compound (III) with a halogenating agent. As the halogenating agent, mention may be made of thionyl chloride, phosphorus pentachloride, phosphorus trichloride, phosphorus tribromide and the like.

Then, Compound (Ia) is obtained by reacting Compound (IV) with an amine represented by the formula (V):

in which $R^4$ and $R^5$ have the same meaning as previously defined.

Compound (V) is used in an amount of 0.1 to 10 equivalents, preferably 0.5 to 3 equivalents, based on Compound (IV). As the reaction solvent, there can be used water, in addition to those mentioned hereinabove. The reaction is carried out at a temperature of from −20° C. to the boiling point of the reaction solvent used and terminates in 30 minutes to 48 hours. If desired, the reaction is carried out in the presence of a base such as those described hereinabove.

Compound (Ic) which is Compound (I) in which $R^1$ and $R^2$ are lower alkyl, aralkyl or lower alkoxymethyl and $R^3$ is

where $R^{61}$ is the other group denoted by $R^6$ than hydrogen, and $R^{5a}$ has the same meaning as previously defined, is prepared form Compound (VI) in accordance with the following reaction steps:

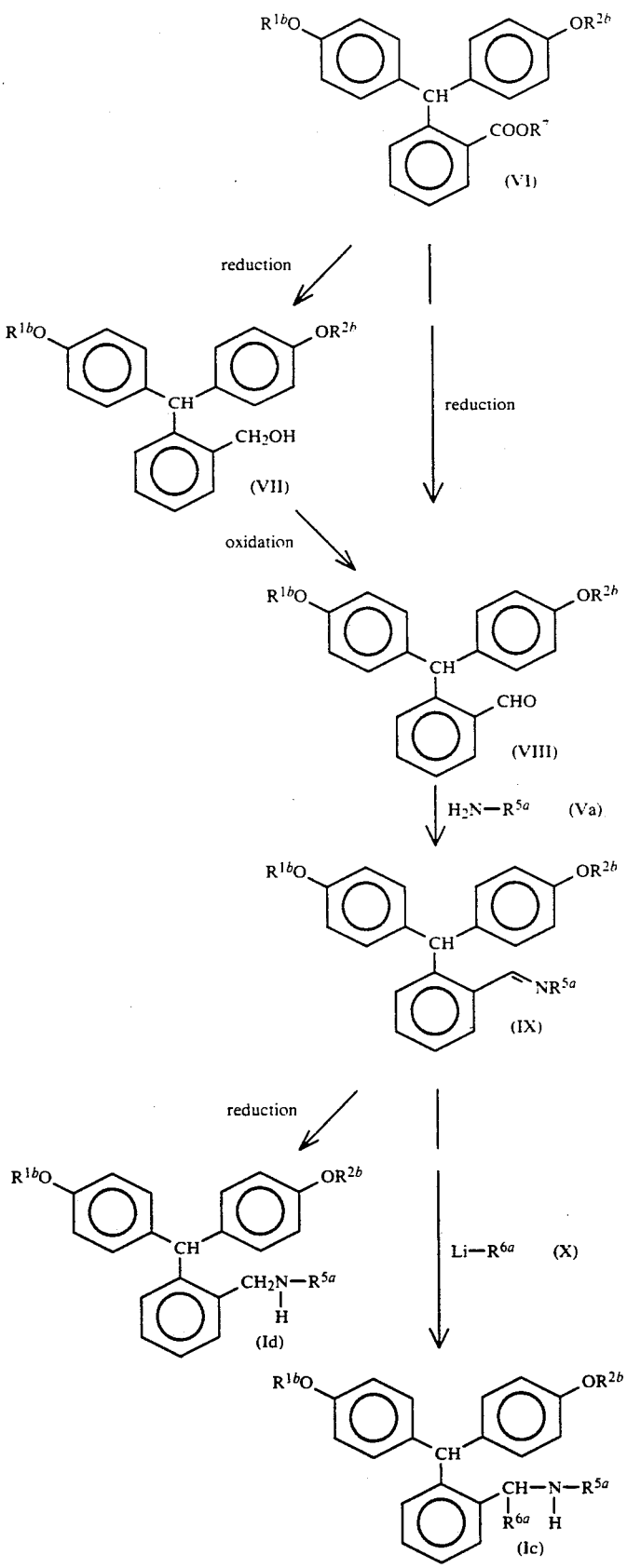
in which $R^{1b}$, $R^{2b}$, $R^{5a}$, $R^{6a}$ and $R^7$ have the same meanings as previously defined.
Compound (VII) is prepared by reducing Compound (VI). As the reducing agent, mention may be made of lithium aluminum hydride, 9-borabicyclo[3.3.1]nonane, lithium triethyl borohydride, aluminum hydride, lithium trimethoxyaluminum hydride and the like.

Compound (VIII) is prepared by oxidizing Compound (VII). As the oxidizing agents usable therefor, mention may be made of Jones oxidation reagent Swern oxidation reagent and Corey-Kim oxidation reagent as well as pyridinium chlorochromate, pyridinium dichromate, manganese dioxide, silver oxide, ruthenium oxide and the like.

Compound (VIII) is obtained by directly reducing Compound (VI). As the, reducing agent usable therefor, mention may be made of diisobutylaluminum hydride and the like.

Compound (IX) is prepared by reacting Compound (VIII) with Compound (Va) represented by the formula (Va).

$$H_2N-R^{5a} \quad (Va)$$

where $R^{5a}$ has the same meaning as previously defined.

Compound (Va) is used in an amount of 0.1 to 10 equivalents, preferably 0.5 to 3 equivalents, based on Compound (VIII). The reaction solvent includes water and those described hereinabove. The reaction is carried out at a temperature of $-20°$ C. to the boiling point of the solvent used and terminates in 30 minutes to 48 hours. If desired, the reaction proceeds in the presence of a base such as those mentioned hereinabove.

Compound (Ic) is prepared by reacting Compound (IX) with Compound (X) represented by the following formula:

$$Li-R^{6a} \quad (X)$$

in which $R^{6a}$ have the same meaning as previously defined.

Any reaction solvent is used alone or in combination, so long as it does not participate in the reaction. The reaction solvent includes, for example, hydrocarbons such as n-hexane, n-pentane, n-heptane and cyclohexane; ethers such as diethyl ether, tetrahydrofuran and dioxane; aromatic hydrocarbons such as toluene and benzene. Usually, the reaction is carried out at a temperature of $-78°$ C. to the boiling point of the solvent used and terminates in 30 minutes to 24 hours.

Compound (Id), which is Compound (I) where $R^1$ and $R^2$ are lower alkyl, aralkyl or alkoxymethyl and $R^3$ is $-CH_2NHR^{5a}$ is prepared by reducing Compound (IX). As the reducing agents usable therefor, mention may be made of complexes of metal hydrides such as aluminum hydride, sodium borohydride and sodium cyanoborohydride. Compound (Id) is also prepared directly, from Compound (VIII), by subjecting Compound (VIII) to amination under a reducing condition.

Compound (Ie) or (If), which is Compound (I) where $R^1$ and $R^2$ are lower alkyl or lower alkanoyl and $R^3$ is $$-\underset{\underset{R^6}{|}}{N}COR^{4b}$$

is prepared in accordance with the following reaction steps from Compound (XI) which is prepared according to the process of J.C.S. Perkin I, 1978, 1211.

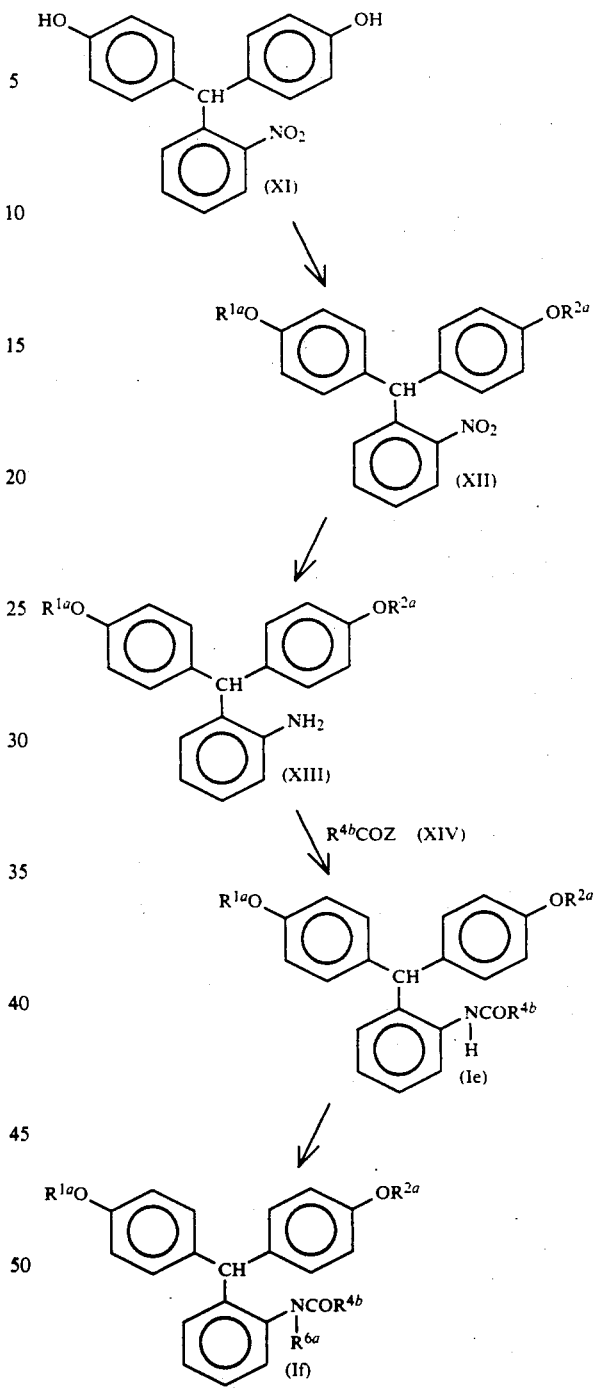

in which $R^{1a}$, $R^{2a}$, $R^{4b}$, $R^{6a}$ and Z have the same meanings as previously defined.

Compound (XII) is prepared by subjecting Compound (XI) to alkylation, aralkylation, alkoxymethylation or acylation in a similar manner as described hereinabove.

Compound (XIII) is prepared by reducing Compound (XII). The reduction reaction is carried out by any of the conventional methods for reducing nitro group to amino group. For example, the reaction is carried out by using a combination of a metal such as tin, iron, zinc, etc., and an acid such as an mineral acid (e.g., hydrochloric acid or sulfuric acid) or organic acids (e.g., acetic acid), or by using sulfides or hydrazines. It can also be carried out catalytically, using a catalyst, such as palladium-carbon and the like.

In case of using a catalyst, the reaction is effected by allowing Compound (XII) to adsorb 3 equivalents of hydrogen in water or a lower alcohol (e.g., methanol, ethanol, etc.) or a mixture thereof, at a temperature of 0° C. to the boiling point of the reaction solvent used. The reaction usually terminates in 30 minutes to 48 hours.

Compound (Ie) is prepared by reacting Compound (XIII) with Compound (XIV) represented by the following formula:

$$R^{4b}COZ \qquad (XIV)$$

in which $R^{4b}$ and Z have the same meanings as previously defined.

Compound (XIV) is readily prepared by the halogenation of a corresponding carboxylic acid, $R^{4b}COOH$. As the halogenating agent usable therefor, mention may be made of thionyl chloride, phosphorus pentachloride, phosphorus trichloride, phosphorus tribromide and the like. Compound (XIV) is used in an amount of from 0.1 to 10 equivalents, preferably from 0.5 to 3 equivalents based on Compound (XIII). As the reaction solvent, mention may be made of water as well as those solvents described hereinabove. The reaction is carried out at a temperature of −20° C. to the boiling point of the solvent and terminates in 30 minutes to 48 hours. If desired, the reaction is carried out in the presence of a base such as those as described hereinbefore.

Compound (If) is prepared by subjecting Compound (Ie) to alkylation in a similar manner as described hereinabove.

Compound (Ib), which is Compound (I) in which $R^1$ and $R^2$ are hydrogen is prepared by hydrolyzing Compound (Ia), (Ic), (Id), (Ie) or (If) where the corresponding $R^{1a}$ or $R^{1b}$, and $R^{2a}$ or $R^{2b}$ are lower alkanoyl in the presence of a base. As the base, there can be used those described hereinabove. As the reaction solvent, water as well as alcohols such as methanol and ethanol can be used alone or in combination. The hydrolysis is carried out at a temperature of 0° C. to the boiling point of the reaction solvent used and terminates in 30 minutes to 24 hours.

Compound (Ib) is also prepared by treating, in an acidic solution, Compound (Ia), (Ic), (Id), (Ie) or (If) in which $R^{1a}$ and $R^{2a}$ are lower alkoxymethyl. The acid usable therefor includes, for example, mineral acids such as hydrochloric acid and sulfuric acid; organic acids such as acetic acid and trifluoroacetic acid, and the like. Usually, the treatment is carried out at a temperature of 0° C. to the boiling point of the reaction solvent used and terminates in 10 minutes to 24 hours.

Compound (Ib) is obtained by reducing Compound (Ia), (Ic), (Id), (Ie) or (If) in which $R^{1a}$ and $R^{2a}$ are aralkyl, with a hydrogenation catalyst such as palladium-carbon and the like, or by treating the compound with a hydrogen bromide-acetic acid solution and the like.

Compound (Ia), (Ic), (Id), (Ie) or (If) where $R^1$ and $R^2$ are lower alkyl is obtained by allowing Compound (Ib) to react with alkylating agent such as those as described hereinabove.

Compound (Ig), which is Compound (Ic) or (Id) where $R^{1b}$ or $R^{2b}$ is lower alkanoyl is synthesized by subjecting Compound (Ib) where $R^3$ is

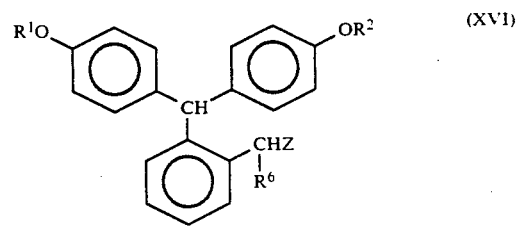

to a similar alkanoylation reaction as described hereinabove.

Compound (Ih) which is Compound (I) where $R^3$ is

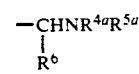

is prepared by reacting Compound (XVI) represented by the following formula:

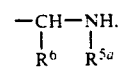

in which $R^1$, $R^2$, $R^6$ and Z have the same meanings as previously defined with Compound (Vb) represented by the following formula:

in which $R^{4a}$ and $R^{5a}$ have the same meanings as previously defined.

Compound (XVI) is prepared by a known process [Arch. Pharm., 292, 690 (1959)] or by processes similar thereto. The reaction of Compound (XVI) with Compound (Vb) is carried out in a reaction solvent similar to those described hereinabove. Usually, it is carried out at a temperature of 0° C. to the boiling point of the reaction solvent and terminates in 1 to 72 hours. If desired, the reaction may be carried out in the presence of the same base as described hereinabove, so as to accelerate the reaction.

The intermediates and the desired products prepared in accordance with the above processes can be isolated and purified by any purification method conventionally employed in the synthetic organic chemistry, e.g., filtration, extraction, washing, drying, concentration, recrystallization, chromatographies and the like. It is also possible to use the intermediates as such in the subsequent reaction step, without subjecting them to any purification.

In the case where Compound (I) is obtained in a free form and its salt form is desired to obtain the free form may be converted into a salt form by a conventional method. In the case where Compound (I) is obtained in a salt form and the salt form is desired to obtain, the salt form as it is can be subjected to a purification step.

Compound (I) and pharmaceutically acceptable salts thereof may be present in the form of an adduct of water or various solvents. The adducts are also included in the scope of the present invention.

Typical examples of Compound (I) obtainable in accordance with the above-mentioned processes are shown in Table 1.

TABLE 1

| Compound No. (Example No.) | R¹ | R² | R³ |
|---|---|---|---|
| 1 (15) | H | H | —CONH—C₆H₄—OCH₃ (3-methoxyphenyl) |
| 2 (1) | CH₃CO | CH₃CO | —CONH—C₆H₃(OCH₃)₂ (2,4-dimethoxyphenyl) |
| 3 (8) | H | H | " |
| 4 (2) | CH₃CO | CH₃CO | —CON(piperidinyl) |
| 5 (9) | H | H | " |
| 6 (75) | (CH₃)₂CH | (CH₃)₂CH | —CON(piperidinyl) |
| 7 (3) | CH₃CO | CH₃CO | —CON(piperazinyl)-N—C₆H₄—OCH₃ (2-methoxyphenyl) |
| 8 (10) | H | H | " |
| 9 (74) | (CH₃)₂CH | (CH₃)₂CH | " |
| 10 (4) | CH₃CO | CH₃CO | —CON(piperazinyl)-N—C₆H₄—OCH₃ (3-methoxyphenyl) |
| 11 (11) | H | H | " |
| 12 (5) | CH₃CO | CH₃CO | —CON(piperazinyl)-N—C₆H₄—OCH₃ (4-methoxyphenyl) |
| 13 (12) | H | H | " |
| 14 (6) | CH₃CO | CH₃CO | —CONH(CH₂)₃—N(morpholinyl)O |
| 15 (13) | H | H | —CONH(CH₂)₃—N(morpholinyl)O |

TABLE 1-continued

| Compound No. (Example No.) | R¹ | R² | R³ |
|---|---|---|---|
| 16 (16) | '' | '' | —CONHCH₂—[pyrrolidine with N-C₂H₅] |
| 17 (17) | '' | '' | —CONH(CH₂)₃—N[2-methylpiperidine] |
| 18 (7) | CH₃CO | CH₃CO | —CONH—[benzothiazol-2-yl] |
| 19 (14) | H | H | —CONH—[benzothiazol-2-yl] |
| 20 (18) | '' | '' | —CONH—[4-phenylthiazol-2-yl] |
| 21 (19) | '' | '' | —CONH—[1-adamantyl] |
| 22 (20) | '' | '' | —CON[4-(2-chlorophenyl)piperazin-1-yl] |
| 23 (21) | '' | '' | —CONH—[9-fluorenyl] |
| 24 (22) | '' | '' | —CONH—[2-adamantyl] |
| 25 (23) | '' | '' | —CONH—[cyclooctyl] |

TABLE 1-continued

| Compound No. (Example No.) | R¹ | R² | R³ |
|---|---|---|---|
| 26 (24) | " | " | —CONH—(benzothiazole-2-yl with 6-OC₂H₅) |
| 27 (25) | H | H | —CONH—(indan-1-yl) |
| 28 (26) | " | " | —CONH—(2-benzoylphenyl) |
| 29 (27) | " | " | —CONHCH(C₆H₅)₂ |
| 30 (28) | " | " | —CON(piperazine)N—COOC₂H₅ |
| 31 (29) | " | " | —CONH—(2-(bis(4-hydroxyphenyl)methyl)phenyl) |
| 32 (30) | " | " | —CONH—(1-benzylpiperidin-4-yl) |
| 33 (31) | " | " | —CONH—(6-(4-tert-butylphenoxy)pyridin-3-yl), —C(CH₃)₃ |
| 34 (32) | H | H | —CONH—(6-(4-bromophenoxy)pyridin-3-yl) |

TABLE 1-continued

| Compound No. (Example No.) | R¹ | R² | R³ |
|---|---|---|---|
| 35 (33) | " | " | —CONH-(pyridyl-O-(2,6-dimethyl-4-chlorophenyl)) |
| 36 (34) | " | " | —CONH-adamantyl |
| 37 (35) | " | " | —CON(morpholino) |
| 38 (36) | " | " | —CON(piperazinyl-N-(3-chlorophenyl)) |
| 39 (37) | " | " | —CON((CH$_2$)$_3$CH$_3$)$_2$ |
| 40 (38) | " | " | —CONH-(5-chloro-2-methylphenyl) |
| 41 (39) | " | " | —CON(3-azaspiro[5.5]undecanyl) |
| 42 (40) | H | H | —CONH-(3-SCH$_3$-phenyl) |
| 43 (41) | " | " | —CON(piperazinyl-N-CH$_2$-phenyl) |
| 44 (42) | " | " | —CONH-(4-F-phenyl) |
| 45 (43) | " | " | —CONH-(4-(CH$_2$)$_3$CH$_3$-phenyl) |

TABLE 1-continued

| Compound No. (Example No.) | R¹ | R² | R³ |
|---|---|---|---|
| 46 (44) | " | " | —CON⟨ ⟩S (thiomorpholine ring) |
| 47 (45) | " | " | —CONHCH₂CH=CH₂ |
| 48 (46) | " | " | —CONH-cyclopentyl |
| 49 (47) | " | " | —CONH(CH₂)₂CH₃ |
| 50 (48) | " | " | —CON(C₂H₅)(3-methylphenyl) |
| 51 (49) | " | " | —CONH-(3-CF₃-phenyl) |
| 52 (50) | H | H | —CONH-(2-iPr-phenyl) |
| 53 (51) | " | " | —CON(CH₃)-phenyl |
| 54 (52) | " | " | —CONH-cyclopropyl |
| 55 (53) | " | " | —CON⟨ ⟩N—CH₃ (4-methylpiperazine) |
| 56 (54) | " | " | —CON⟨ ⟩=O (4-oxopiperidine) |
| 57 (55) | " | " | —CONH(CH₂)₂N(CH₃)₂·HCl |
| 58 (56) | " | " | —CON⟨ ⟩ (tetrahydropyridine) |
| 59 (57) | " | " | —CONH(CH₂)₂OC₂H₅ |
| 60 (58) | " | " | —CONH-norbornyl |

TABLE 1-continued
| Compound No. (Example No.) | R¹ | R² | R³ |
|---|---|---|---|
| 61 (59) | " | " | —CONHCH$_2$CF$_3$ |
| 62 (60) | H | H | —CONH—⟨C$_6$H$_4$⟩—(CH$_2$)$_2$CH$_3$ 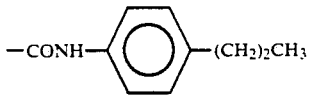 |
| 63 (61) | " | " | —CONH-indanyl 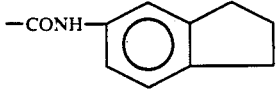 |
| 64 (62) | " | " | —CONH—⟨C$_6$H$_4$⟩—N-morpholino 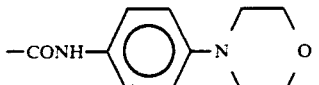 |
| 65 (63) | " | " | —CONH-(pyridyl)-O-(5-chloropyridyl) 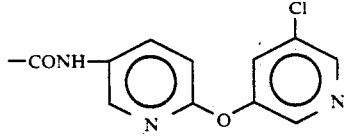 |
| 66 (64) | " | " | —CON(piperazinyl)-phenyl 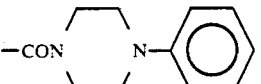 |
| 67 (65) | " | " | —CONHC(CH$_3$)$_3$ |
| 68 (66) | " | " | —CONH—⟨C$_6$H$_4$⟩—CH$_3$ (ortho) 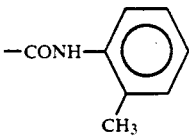 |
| 69 (67) | " | " | —CONH—⟨C$_6$H$_4$⟩—O(CH$_2$)$_3$CH$_3$ 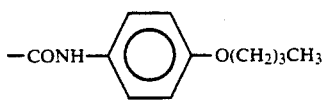 |
| 70 (68) | " | " | —CON(dibenzo) 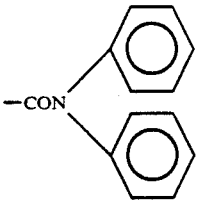 |
| 71 (69) | H | H | —CON(bicyclic) 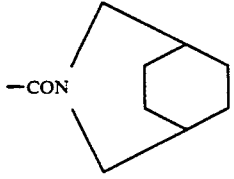 |
| 72 (70) | " | " | —CONHCH$_2$-thienyl 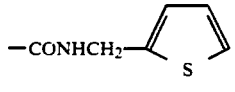 |

TABLE 1-continued
| Compound No. (Example No.) | R¹ | R² | R³ |
|---|---|---|---|
| 73 (71) | " | " | 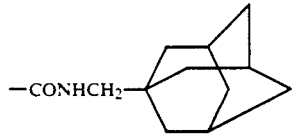 —CONHCH₂— (adamantyl) |
| 74 (72) | " | " | 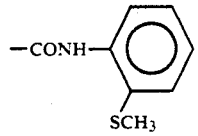 —CONH—(phenyl)—SCH₃ |
| 75 (73) | " | " | 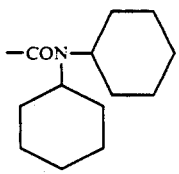 —CON(cyclohexyl)₂ |
| 76 (76) | CH₃OCH₂ | CH₃OCH₂ | 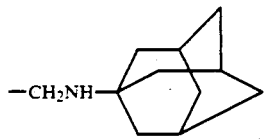 —CH₂NH— (adamantyl) |
| 77 (77) | " | " | 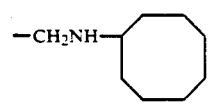 —CH₂NH—(cyclooctyl) |
| 78 (78) | " | " | 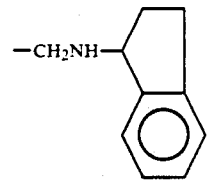 —CH₂NH—(indanyl) |
| 79 (79) | CH₃OCH₂ | CH₃OCH₂ | 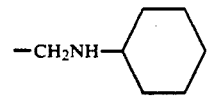 —CH₂NH—(cyclohexyl) |
| 80 (80) | " | " | 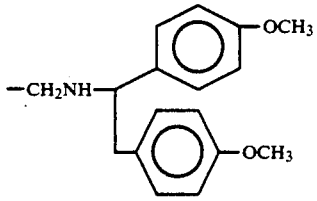 —CH₂NH—CH(4-methoxyphenyl)(4-methoxyphenyl) |
| 81 (81) | " | " | 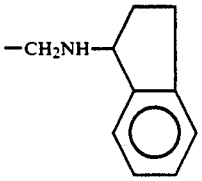 —CH₂NH—(indanyl) |

TABLE 1-continued

| Compound No. (Example No.) | R¹ | R² | R³ |
|---|---|---|---|
| 82 (82) | Ph-CH₂– | Ph-CH₂– | –CH₂NH–(cyclooctyl) |
| 83 (83) | " | " | –CH₂NH–(piperidin-4-yl)-N-CH₂-Ph · 2HCl |
| 84 (84) | H | H | –CH₂NH–(piperidin-4-yl)-N-CH₂-Ph |
| 85 (85) | " | " | –CH₂NH–(cyclooctyl) |
| 86 (86) | H | H | –CH₂NH–(2-adamantyl) |
| 87 (87) | " | " | –CH₂NHCH(Ph)(Ph) · HCl |
| 88 (88) | Ph-CH₂– | Ph-CH₂– | –CH(($CH_2$)$_3$CH$_3$)NH–(piperidin-4-yl)-N-CH₂-Ph · 2HCl |
| 89 (89) | H | H | –CH₂N(piperazinyl)-(2-Cl-Ph) |
| 90 (90) | " | " | –CH₂N(piperazinyl)-(3-OCH₃-Ph) |
| 91 (91) | " | " | –CH₂N(1,2,3,4-tetrahydroquinolin-1-yl) |

TABLE 1-continued

| Compound No. (Example No.) | R¹ | R² | R³ |
|---|---|---|---|
| 92 (92) | " | " | 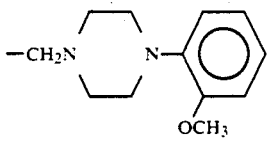 —CH₂N(piperazine)N-phenyl-OCH₃ |
| 93 (93) | H | H | 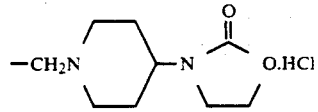 —CH₂N(piperidine)-N-C(=O)-O·HCl (oxazolidinone) |
| 94 (94) | " | " | 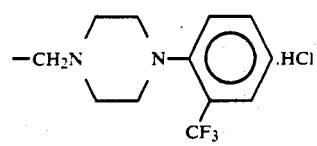 —CH₂N(piperazine)N-phenyl-CF₃ ·HCl |
| 95 (95) | " | " | 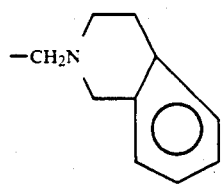 —CH₂N(indoline) |
| 96 (96) | " | " | 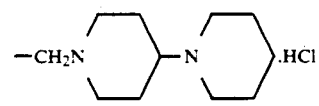 —CH₂N(piperidine)-piperidine ·HCl |
| 97 (97) | " | " | 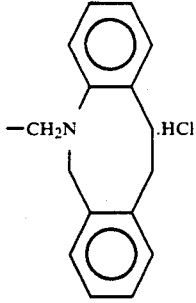 —CH₂N(dibenzazepine) ·HCl |
| 98 (98) | " | " | 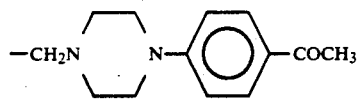 —CH₂N(piperazine)N-phenyl-COCH₃ |
| 99 (99) | " | " | 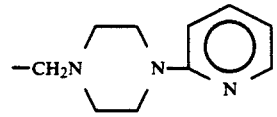 —CH₂N(piperazine)N-(2-pyridyl) |
| 100 (100) | CH₃CO | CH₃CO | 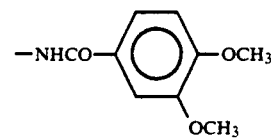 —NHCO-phenyl(OCH₃)(OCH₃) |
| 101 (101) | CH₃CO | CH₃CO | 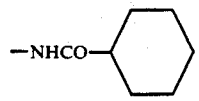 —NHCO-cyclohexyl |

TABLE 1-continued
| Compound No. (Example No.) | R[1] | R[2] | R[3] |
|---|---|---|---|
| 102 (102) | " | " | 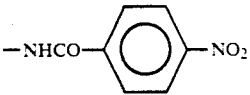 |
| 103 (103) | " | " | 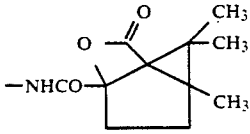 |
| 104 (104) | " | " | 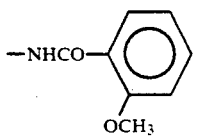 |
| 105 (105) | " | " | 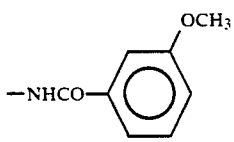 |
| 106 (106) | " | " | 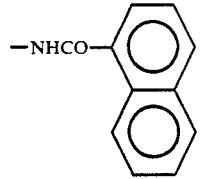 |
| 107 (107) | " | " | 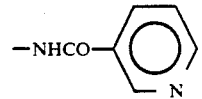 |
| 108 (108) | " | " | 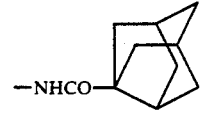 |
| 109 (109) | CH₃CO | CH₃CO | 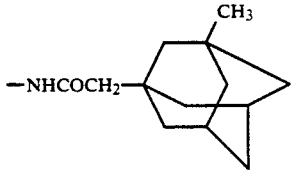 |
| 110 (110) | " | " | 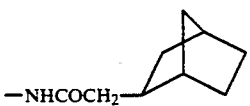 |
| 111 (111) | " | " | 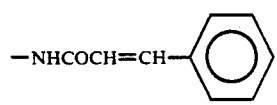 |
| 112 (112) | " | " | —NHCOC(CH₃)₃ |

TABLE 1-continued
| Compound No. (Example No.) | R¹ | R² | R³ |
|---|---|---|---|
| 113 (113) | " | " | 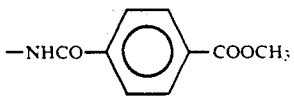 —NHCO—⟨C₆H₄⟩—COOCH₃ |
| 114 (114) | " | " | 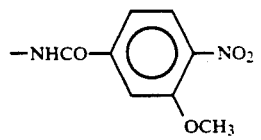 —NHCO—⟨C₆H₃⟩(NO₂)(OCH₃) |
| 115 (115) | " | " | 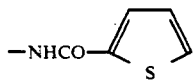 —NHCO—(2-thienyl) |
| 116 (116) | " | " | 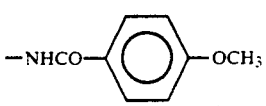 —NHCO—⟨C₆H₄⟩—OCH₃ |
| 117 (117) | H | H | 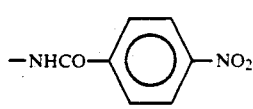 —NHCO—⟨C₆H₄⟩—NO₂ |
| 118 (118) | H | H | 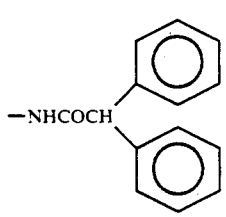 —NHCOCH(C₆H₅)₂ |
| 119 (119) | " | " | 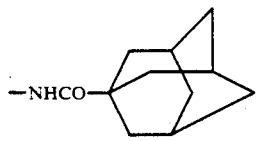 —NHCO—(adamantyl) |
| 120 (120) | " | " | 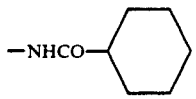 —NHCO—(cyclohexyl) |
| 121 (121) | " | " | 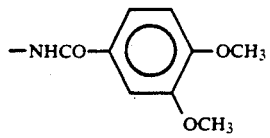 —NHCO—⟨C₆H₃⟩(OCH₃)(OCH₃) |
| 122 (122) | " | " | 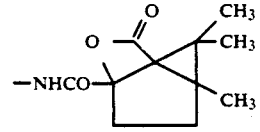 —NHCO—(trimethylcyclopropane lactone) |
| 123 (123) | " | " |  —NHCO—⟨C₆H₄⟩—OCH₃ |

TABLE 1-continued

| Compound No. (Example No.) | R¹ | R² | R³ |
|---|---|---|---|
| 124 (124) | " | " | —NHCO—(3-OCH₃-phenyl) |
| 125 (125) | " | " | —NHCO—(naphthyl) |
| 126 (126) | H | H | —NHCO—(pyridyl)·HCl |
| 127 (127) | " | " | —NHCO—(norbornyl) |
| 128 (128) | " | " | —NHCOCH₂—(methyladamantyl) |
| 129 (129) | " | " | —NHCOCH₂—(norbornyl) |
| 130 (130) | " | " | —NHCOCH=CH—(phenyl) |
| 131 (131) | " | " | —NHCOC(CH₃)₃ |
| 132 (132) | " | " | —NHCO—(4-COOH-phenyl) |
| 133 (133) | " | " | —NHCO—(3-NO₂-4-OCH₃-phenyl) |
| 134 (134) | H | H | —NHCO—(thienyl) |
| 135 (135) | " | " | —NHCO—(4-OCH₃-phenyl) |

TABLE 1-continued

| Compound No. (Example No.) | R$^1$ | R$^2$ | R$^3$ |
|---|---|---|---|
| 136 (136) | " | " | —NHCO—⟨phenyl⟩—NH$_2$ |
| 137 (137) | CH$_3$OCH$_2$ | CH$_3$OCH$_2$ | —NCO(CH$_3$)—⟨cyclohexyl⟩ |
| 138 (138) | H | H | " |

The bone absorption-inhibiting effects of the compounds of the present invention is proved by the following experiment.

Experiment

A calvaria of a 5 to 6 day-old dd mouse was aseptically cut off, washed with Dulbecco's modified phosphate buffered saline not containing calcium and magnesium (manufactured by Gibco Oriental Co.) and separated along the sutura of its center. One half of the calvaria so separated was cultured in 1.5 ml of Dulbecco's modified Eagle medium (manufactured by Gibco Oriental Co.) containing 15% of thermally inactivated (at 56° C. for 20 minutes) horse serum and 2.5% of fetal calf serum. The test compound was dissolved in dimethyl sulfoxide, and 10 μl ($1 \times 10^{-4}$ M) of the solution so prepared was added to the culture. Parathyroid hormone (PTH) was dissolved in 0.15 M sodium chloride solution (pH 3), and 3 μl ($1 \times 10^{-8}$ M) of solution so prepared was added to the culture. The cultivation was carried out for 96 hours at 37° C. in an atmosphere consisting of 95% of air and 5% of carbon dioxide (the culture medium was once replaced with a fresh one after 48 hours from the beginning of the cultivation). The concentration of dissolved calcium (i.e., absorption of bone) from the PTH-intensified bone was determined by measuring the quantity of calcium accumulated in the culture collected in 96 hours of cultivation, whereby the concentration of total calcium contained in the culture was measured with Calcium C-Test Wako (manufactured by Wako Pure Chemicals Co., Ltd.), and the inhibition rate was calculated therefrom in accordance with the equation set forth below. Results obtained are shown in Table 2.

$$\text{Inhibition rate (\%)} = \frac{Cp - Cd}{Cp - Co} \times 100$$

Cd: Total calcium concentration in culture treated with both test compound and PTH
Cp: Total calcium concentration in culture treated with PTH alone
Co: Total calcium concentration in culture treated with neither test compound nor PTH

TABLE 2

| Compound No. | Inhibition Rate (%) |
|---|---|
| 5 | 105.5 |
| 8 | 133.9 |
| 9 | 93.6 |
| 13 | 86.4 |
| 19 | 124.2 |
| 21 | 159.2 |
| 23 | 172.3 |
| 24 | 167.9 |
| 25 | 130.6 |
| 26 | 141.7 |
| 27 | 125.5 |
| 28 | 144.0 |
| 29 | 203.0 |
| 76 | 167.9 |
| 77 | 174.5 |
| 78 | 127.4 |
| 79 | 136.8 |
| 80 | 38.2 |
| 81 | 127.4 |
| 84 | 141.7 |
| 118 | 203.0 |
| 119 | 212.0 |
| 121 | 203.0 |

Compound (I) and pharmaceutically acceptable salts thereof are formulated into any form of conventionally employed preparations, for example, tablets, capsules, syrups, injections, drippings, suppositories, etc., and administered either orally or non-orally, including, e.g., intramuscular injection, intravenous injection, intraarterial injection, dripping, and rectal administration of suppositories. Such preparations are produced by any of the conventional methods and may contain other ingredients, for example, excipients, lubricants, binders, disintegrators, suspending agents, isotonicities, emulsifying agents and the like.

As the carrier to be used in such preparations, mention may be made of water, distilled water for injection, physiological sodium chloride solution, glucose, fructose, sucrose, mannitol, lactose, starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resins, sorbitan fatty acid esters, glycerol fatty acid esters and the like.

Embodiments of the present invention are illustrated by the following examples and reference examples.

EXAMPLE 1

2-[Bis(4-acetoxyphenyl)methyl]-N-(2,4-dimethoxyphenyl)benzamide (Compound 2)

In 20 ml of methylene chloride were dissolved 1.08 g of 2,4-dimethoxyaniline and 4.5 ml of triethylamine. To this solution was dropwise added under ice cooling 20 ml of methylene chloride containing 3 g of 2-[bis(4-acetoxyphenyl)methyl]benzoyl chloride obtained in Reference Example 2. After stirring for 7 hours, water was added thereto. The organic layer was separated off, and the aqueous layer was extracted with chloroform. The chloroform layer was combined with the organic layer, and the combined organic layer was washed with 2N aqueous hydrochloric acid solution and dried over anhydrous magnesium sulfate. The resulting solution was concentrated under reduced pressure to give 2.6 g of the desired product (Compound 2) as an oily matter.

NMR (CDCl$_3$) δ (ppm): 8.25–8.18, 7.60–6.88, 6.60–6.45, 6.17, 3.78, 3.65, 2.25

In the following Examples 2 to 7, desired products were obtained in a similar manner as in Example 1, except that corresponding amines were used in place of 2,4-dimethoxyaniline.

EXAMPLE 2

1-{2-[Bis(4-acetoxyphenyl)methyl]benzoyl}piperidine (Compound 4)

NMR (CDCl$_3$) δ (ppm): 7.25–6.90, 5.93, 3.95–1.45

EXAMPLE 3

1-{2-[Bis(4-acetoxyphenyl)methyl]benzoyl}-4-(2-methoxyphenyl)piperazine (Compound 7)

NMR (CDCl$_3$) δ (ppm): 7.35–6.76, 6.01, 3.95–1.65

EXAMPLE 4

1-{2-[Bis(4-acetoxyphenyl)methyl]benzoyl}-4-(3-methoxyphenyl)piperazine (Compound 10)

NMR (CDCl$_3$) δ (ppm): 7.32–6.94, 6.50–6.39, 6.00, 3.95–1.60

EXAMPLE 5

1-{2-[Bis(4-acetoxyphenyl)methyl]benzoyl}-4-(4-methoxyphenyl)piperazine (Compound 12)

NMR (CDCl$_3$) δ (ppm): 7.25–6.83, 6.01, 3.88–3.76, 3.20–1.80

EXAMPLE 6

2-[Bis(4-acetoxyphenyl)methyl]-N-(3-morpholinopropyl)benzamide (Compound 14)

NMR (CDCl$_3$) δ (ppm): 7.28–6.89, 6.35, 3.63–3.04, 2.42–2.27, 2.67–2.30

EXAMPLE 7

2-[Bis(4-acetoxyphenyl)methyl]-N-(benzothiazol-2-yl)benzamide (Compound 18)

NMR (CDCl$_3$) δ (ppm): 7.48–6.80, 5.95, 2.27

EXAMPLE 8

2-[Bis(4-hydroxyphenyl)methyl]-N-(2,4-dimethoxyphenyl)benzamide (Compound 3)

In a mixture of 50 ml of saturated aqueous sodium hydrogencarbonate solution and 50 ml of methanol was suspended 2.6 g of Compound 2 prepared in Example 1, and the suspension was heated under reflux for 30 minutes. The resulting mixture was concentrated under reduced pressure, and water was added to the residue. The resulting mixture was extracted with ethyl acetate, and the extract was dried over anhydrous magnesium sulfate. After concentration under reduced pressure, the residue was recrystallized to afford 1.23 g of the desired product.

Melting point: 122.5–124.0° C.
IR (KBr) cm$^{-1}$: 1644, 1510, 1208
NMR (DMSO-d$_6$) δ (ppm): 8.60, 8.16, 7.54–7.09, 6.90–6.40, 5.88, 3.79, 3.64

In the following Examples 9 to 14, the desired products were obtained in a similar manner as in Example 8, except that corresponding acetyl derivatives were employed.

EXAMPLE 9

1-{2-[Bis(4-hydroxyphenyl)methyl]benzoyl}piperidine (Compound 5)

Melting point: 242.0–244.0° C.
IR (KBr) cm$^{-1}$: 1603, 1583, 1511
NMR (DMSO-d$_6$) δ (ppm): 9.14, 7.30–6.60, 5.51, 3.41–3.18, 1.41–1.31

EXAMPLE 10

1-{2-[Bis(4-hydroxyphenyl)methyl]benzoyl}-4-(2-methoxyphenyl)piperazine (Compound 8)

Melting point: 229.0–231.0° C.
IR (KBr) cm$^{-1}$: 1608, 1583, 1505
NMR (DMSO-d$_6$+CDCl$_3$) δ (ppm): 8.83, 8.72, 7.21–6.62, 5.74, 3.81, 3.81–2.61

EXAMPLE 11

1-{2-[Bis(4-hydroxyphenyl)methyl]benzoyl}-4-(3-methoxyphenyl)piperazine (Compound 11)

Melting point: 229.0–234.0° C.
IR (KBr) cm$^{-1}$: 1605, 1597, 1509
NMR (DMSO-d$_6$) δ (ppm): 9.25, 9.19, 7.35–7.17, 7.07–6.65, 5.62, 3.74, 3.68–3.00, 2.65–2.50, 1.93

EXAMPLE 12

1-{2-[Bis(4-hydroxyphenyl)methyl]benzoyl}-4-(4-methoxyphenyl)piperazine (Compound 13)

Melting point: 208.0–210.0° C.
IR (KBr) cm$^{-1}$: 1646, 1610, 1511
NMR (DMSO-d$_6$) δ (ppm): 7.57–6.71, 5.92, 4.0–2.5, 3.82

EXAMPLE 13

2-[Bis(4-hydroxyphenyl)methyl]-N-(3-morpholinopropyl)benzamide (Compound 15)

Melting point: 120.0–121.5° C.
IR (KBr) cm$^{-1}$: 1643, 1511, 1237
NMR (DMSO-d$_6$) δ (ppm): 9.25, 8.11, 7.30–6.62, 5.91, 3.67–3.09, 2.27–2.17, 1.47

EXAMPLE 14

N-(Benzothiazol-2-yl)-2-[bis(4-hydroxyphenyl)methyl]benzamide (Compound 19)

Melting point: 139.5–141.0° C.
IR (KBr) cm$^{-1}$: 1644, 1537, 1504
NMR (DMSO-d$_6$) δ (ppm): 9.20, 8.00–7.04, 6.84–6.61, 5.94

EXAMPLE 15

2-[Bis(4-hydroxyphenyl)methyl]-N-(3-methoxyphenyl)benzamide (Compound 1)

In 20 ml of methylene chloride were dissolved 0.62 g of m-anisidine and 5 ml of triethylamine. To this solution was added dropwise under ice cooling 20 ml of methylene chloride containing 2.64 g of 2-[bis(4-acetoxyphenyl)methyl]benzoyl chloride as obtained in Reference Example 2. After stirring for 30 minutes, water was added thereto. The organic layer was separated off, and the water layer was extracted with chloroform. The chloroform layer was combined with the organic layer, and the combined organic layer was washed with 2N aqueous hydrochloric acid solution and dried over anhydrous magnesium sulfate. The organic layer was concentrated under reduced pressure, and the residue was suspended in a mixture of 50 ml of saturated aqueous sodium hydrogencarbonate solution and 50 ml of methanol, and the resulting suspension was heated under reflux for 2 hours. The suspension was concentrated under reduced pressure, and water was added to the residue. The resulting mixture was extracted with ethyl acetate, and the extract was dried over anhydrous magnesium sulfate. The residue was concentrated under reduced pressure, and was recrystallized to afford 1.54 g of the desired product.

Melting point: 106–107° C.
IR (KBr) cm$^{-1}$: 1645, 1600, 1509
NMR (DMSO-d$_6$) δ (ppm): 10.18, 9.20, 7.40–7.04, 6.86–6.62, 5.87, 3.73

In the following Examples 16 to 73, desired products were obtained in a similar manner as in Example 15, except that corresponding amines were used in place of m-anisidine.

EXAMPLE 16

N-(1-Ethylpyrrolidin-2-yl)methyl]-2-[bis(4-hydroxyphenyl)methyl]benzamide (Compound 16)

Melting point: 229.0–230.0° C.
IR (KBr) cm$^{-1}$: 1638, 1509, 1170
NMR (DMSO-d$_6$) δ (ppm): 9.19, 8.93, 7.33–6.97, 6.82–6.61, 5.92, 3.0–2.04, 1.61–1.37, 1.0

EXAMPLE 17

2-[Bis(4-hydroxyphenyl)methyl]-N-[3-(2-methylpiperidino)propyl]benzamide (Compound 17)

Melting point: 118.0–120.0° C.
IR (KBr)·cm$^{-1}$: 1638, 1511, 1240
NMR (DMSO-d$_6$) δ (ppm): 9.19, 8.16, 7.33–6.62, 5.89, 3.14–2.15, 1.51–1.2, 0.94

EXAMPLE 18

2-[Bis(4-hydroxyphenyl)methyl]-N-(4-phenylthiazol-2-yl)benzamide (Compound 20)

Melting point: 291.0–292.5° C.
IR (KBr) cm$^{-1}$: 1678, 1651, 1537
NMR (DMSO-d$_6$) δ (ppm): 12.58, 9.21, 7.92–7.04, 6.84–6.62, 5.95

EXAMPLE 19

N-(Tricyclo[3.3.1.1$^{3,7}$]dec-1-yl)-2-[bis(4-hydroxyphenyl)methyl]benzamide (Compound 21)

Melting point 167–169° C.
IR (KBr) cm$^{-1}$: 1631, 1514, 1269
NMR (DMSO-d$_6$) δ (ppm): 7.43, 7.29–7.18, 6.97, 6.85–6.63, 5.83, 1.97–1.92, 1.65–1.43

EXAMPLE 20

1-(2-Chlorophenyl)-4-{2-[bis(4-hydroxyphenyl)methyl]benzoyl}piperazine (Compound 22)

Melting point: >300° C.
IR (KBr) cm$^{-1}$: 1610, 1574, 1511
NMR (DMSO-d$_6$) δ (ppm): 9.28, 9.20, 7.39–7.18, 7.07–6.90, 6.85–6.65, 5.65, 3.91–3.86, 3.52–3.45, 3.23–3.00, 2.66–2.48, 1.81–1.06

EXAMPLE 21

N-(9-Fluorenyl)-2-[bis(4-hydroxyphenyl)methyl]benzamide (Compound 23)

NMR (DMSO-d$_6$) δ (ppm): 9.20, 8.73, 7.80, 7.41–7.20, 6.97–6.67, 6.29, 6.10

EXAMPLE 22

N-(Tricyclo[3.3.1.1$^{3,7}$]dec-2-yl)-2-[bis(4-hydroxyphenyl)methyl]benzamide (Compound 24)

NMR (DMSO-d$_6$) δ (ppm): 9.12, 7.81, 7.32–7.21, 6.97, 6.83–6.61, 5.84, 3.93, 1.88–1.36

EXAMPLE 23

N-Cyclooctyl-2-[bis(4-hydroxyphenyl)methyl]benzamide (Compound 25)

NMR (DMSO-d$_6$) δ (ppm): 9.12, 7.89, 7.31–7.19, 6.96, 6.83–6.62, 5.89, 3.93, 1.88–1.36

EXAMPLE 24

N-(6-Ethoxybenzothiazol-2-yl)-2-[bis(4-hydroxyphenyl)methyl]benzamide (Compound 26)

NMR (DMSO-d$_6$) δ (ppm): 12.50, 9.21, 7.63–7.33, 7.04, 6.84–6.61, 5.94, 4.08, 1.36

EXAMPLE 25

2-[Bis(4-hydroxyphenyl)methyl]-N-(1-indanyl)benzamide (Compound 27)

NMR (DMSO-d$_6$) δ (ppm): 9.18, 8.42, 7.35–6.04, 6.10, 5.38, 2.92–2.70, 2.31, 1.80

EXAMPLE 26

N-(2-Benzoylphenyl)-2-[bis(4-hydroxyphenyl)methyl]benzamide (Compound 28)

NMR (DMSO-d$_6$) δ (ppm): 10.3, 9.13, 7.71–6.59, 5.75

EXAMPLE 27

2-[Bis(4-hydroxyphenyl)methyl]-N-diphenylmethylbenzamide (Compound 29)

NMR (DMSO-d$_6$) δ (ppm): 9.58, 9.15, 7.33–7.07, 6.85–6 57, 5.55, 5.13

EXAMPLE 28

1-Ethoxycarbonyl-4-{2-[bis(4-hydroxyphenyl)methyl]benzoyl}piperazine (Compound 30)

NMR (DMSO-d$_6$) δ (ppm): 9.23, 9.19, 7.32–7.15, 6.98, 6.82–6.65, 5.56, 4.02, 3.48–2.85, 2.50–2.34

EXAMPLE 29

2-[Bis(4-hydroxyphenyl)methyl]-N-{2-[bis(4-hydroxyphenyl)phenyl}benzamide (Compound 31)

NMR (DMSO-d$_6$) δ (ppm): 9.45, 9.15, 7.35–6.97, 6.89–6.63, 5.94, 5.72

EXAMPLE 30

N-{4-(1-Benzylpiperidyl)}-2-[bis(4-hydroxyphenyl)methyl]benzamide (Compound 32)

NMR (DMSO-d$_6$) δ (ppm): 10.21, 9.19, 8.26, 7.56–7.23, 6.96, 6.82–6.63, 5.89, 4.24–3.84, 3.35–2.90, 2.00–1.60

EXAMPLE 31

N-[2-(4-tert-Butylphenoxy)pyridin-5-yl]-2-[bis(4-hydroxyphenyl)methyl]benzamide (Compound 33)

Melting point: 121 –125° C.
IR (KBr) cm$^{-1}$: 3300, 1715, 1644, 1594, 1511, 1482, 377, 1257, 1170, 1107, 1014, 890, 814
NMR (DMSO-d$_6$) δ (ppm): 10.24, 9.15, 8.27, 8.01, 7.50–7.30, 7.10–6.95, 6.84, 6.64, 5.90, 1.30

EXAMPLE 32

N-[2-(4-Bromophenoxy)pyridin-5-yl]-2-[bis(4-hydroxyphenyl)methyl]benzamide (Compound 34)

Melting point: 218 –223° C.
IR (KBr) cm$^{-1}$: 3300, 1712, 1650, 1598, 1538, 1512, 479, 1313, 1254, 1170, 1070, 1011, 889, 833, 784, 743
NMR (DMSO-d$_6$) δ (ppm): 10.27, 9.16, 8.29, 8.04, 7.57, 5 7.50–7.25, 7.15–7.00, 6.84, 6.64, 5.89

EXAMPLE 33

N-[2-(4-Chloro-3,5-dimethylphenoxy)pyridin-5-yl]-2-(bis-(4-hydroxyphenyl)methyl]benzamide (Compound 35)

Melting point: 125° C. (Decomposed)
IR (KBr) cm$^{-1}$: 3300, 1650, 1594, 1511, 1484, 1465, 379, 1303, 1236, 1170, 1148, 1104, 1026, 823,
NMR (DMSO-d$_6$) δ (ppm): 10.26, 9.16, 8.29, 8.03, 7.50–7.30, 7.10–7.00, 6.95, 6.84, 6.64, 5.90, 2.33

EXAMPLE 34

N-(Tricyclo[3.3.1.0$^{3,7}$]non-3-yl)-2-[bis(4-hydroxyphenyl)methyl]benzamide (Compound 36)

Melting point: 219–224° C.
IR (KBr) cm$^{-1}$: 3200, 2938, 1659, 1627, 1598, 1512, 477, 1325, 1258, 1231, 1176, 825, 740
NMR (DMSO-d6) δ (ppm): 9.14, 7.90, 7.35–7.15, 6.95, 6.82, 6.65, 5.90, 2.36, 2.17, 2.05–1.70, 1.60–1.40

EXAMPLE 35

4-{2-[Bis(4-hydroxyphenyl)methyl]benzoyl}morpholine (Compound 37)

NMR (DMSO-d$_6$) δ (ppm): 9.25, 9.19, 7.35–7.14, 6.97, 6.81–6.65, 5.59, 3.58–3.19, 2.89, 2.57, 2.35–2.28

EXAMPLE 36

1-(3-Chlorophenyl)-4-[2-[bis(4-hydroxyphenyl)methylbenzoylpiperazine (Compound 38)

NMR (DMSO-d6) δ (ppm): 9.20, 7.36–7.15, 7.00, 5.59, 3.61, 3.05–3.01, 2.88–2.78, 2.55–2.48, 2.33–2.25

EXAMPLE 37

N,N-Dibutyl-2-[bis(4-hydroxyphenyl)methyl]benzamide (Compound 39)

NMR (DMSO-d$_6$) δ (ppm): 9.26, 7.33–6.98, 6.86–6.57, 5.46, 3.45–3.12, 2.60–2.45, 1.45–0.60

EXAMPLE 38

N-(5-Chloro-2-methylphenyl)-2-[bis(4-hydroxyphenyl)-methyl]benzamide (Compound 40)

NMR (DMSO-d$_6$) δ (ppm): 9.21, 7.42–6.60, 6.00, 2.10

EXAMPLE 39

3-{2-[Bis(4-hydroxyphenyl)methyl]benzoyl}-3-azaspiro[5.5]undecan (Compound 41)

NMR (DMSO-d$_6$) δ (ppm): 7.31–6.61, 5.58, 3.50–3.28, 2.80–2.70, 2.46–2.25, 1.35–1.10

EXAMPLE 40

2-[Bis(4-hydroxyphenyl)methyl]-N-(3-thiomethylphenyl)benzamide (Compound 42)

NMR (DMSO-d6) δ (ppm): 9.20, 7.60, 7.45–7.21, 7.12, 6.98–6.62, 5.93, 2.44

EXAMPLE 41

1-Benzyl-4-{2-[bis(4-hydroxyphenyl)methyl]benzoyl}piperazine (Compound 43)

NMR (DMSO-d$_6$) δ (ppm): 7.23–6.79, 5.63, 3.60–3.30, 2.85–2.80, 2.50–1.95

EXAMPLE 42

N-(4-Fluorophenyl)-2-[bis(4-hydroxyphenyl)methyl]benzamide (Compound 44)

Melting point: 122 –124° C.
IR (KBr) cm$^{-1}$: 3320, 1650, 1615, 1515
NMR (DMSO-d6) δ (ppm): 10.13, 7.80–6.90, 6.85–6.20, 5.86

EXAMPLE 43

N-(4-Butylphenyl)-2-[bis(4-hydroxyphenyl)methyl]benzamide (Compound 45)

Melting point: 119 –121° C.
IR (KBr) cm$^{-1}$: 3300, 2920, 1600, 1520
NMR (DMSO-d$_6$) δ (ppm): 10.00, 9.03, 7.55–6.90, 6.85–6.45, 5.83, 2.65–2.35, 1.80–1.70

EXAMPLE 44

4-{2-[Bis(4-hydroxyphenyl)methyl]benzoyl}thiomorpholine (Compound 46)

Melting point: 259 –261° C.
IR (KBr) cm$^{-1}$: 3300, 1605, 1590, 1510
NMR (DMSO-d$_6$) δ (ppm): 9.30–9.00, 7.35–6.45, 5.48, 3.90–3.00, 2.90–2.40

EXAMPLE 45

N-Allyl-2-[bis(4-hydroxyphenyl)methyl]benzamide (Compound 47)

Melting point: 179 –181° C.
IR (KBr) cm$^{-1}$: 3350, 3170, 1630, 1600, 1515
NMR (DMSO-d$_6$) δ (ppm): 9.03, 8.25–8.00, 7.35–7.05, 7.00–6.45, 5.95–5.40, 5.15–4.75, 3.85–3.55

EXAMPLE 46

N-Cyclopentyl-2-[bis(4-hydroxyphenyl)methyl]benzamide (Compound 48)

Melting point 148 –150° C.
IR (KBr) cm$^{-1}$: 3150, 1635, 1515
NMR (DMSO-d6) δ (ppm): 9.05, 7.97–7.70, 7.35–6.40, 5.83, 4.15–3.85, 1.90–1.15

EXAMPLE 47

2-[Bis(4-hydroxyphenyl)methyl]-N-propylbenzamide (Compound 49)

Melting point: 202° C.
IR (KBr) cm$^{-1}$: 3330, 1630, 1615, 1515

NMR (DMSO-d6) δ (ppm): 9.07, 8.10–7.85, 7.50–7.10, 7.05–6.45, 5.90, 3.35–2.95, 1.55–0.65

EXAMPLE 48

N-Ethyl-2-[bis(4-hydroxyphenyl)methyl]-N-(3-methylphenyl)benzamide (Compound 50)

Melting point: 218 –220° C.
IR (KBr) cm$^{-1}$: 3280, 1615, 1580, 1515
NMR (DMSO-d$_6$) δ (ppm): 9.15, 7.45–6.15, 5.85, 3.90–3.70, 2.05, 1.25–0.90

EXAMPLE 49

N-(3-Trifluoromethylphenyl)-2-[bis(4-hydroxyphenyl)methyl]benzamide (Compound 51)

Melting point: 198 –200° C.
IR (KBr) cm$^{-1}$: 3320, 1640, 1600, 1515, 1445
NMR (DMSO-d$_6$) δ (ppm): 10.40, 8.10–7.15, 7.10–6.40, 5.86

EXAMPLE 50

2-[Bis(4-hydroxyphenyl)methyl]-N-(2-isopropylphenyl)benzamide (Compound 52)

Melting point: 225 –227° C.
IR (KBr) cm$^{-1}$: 3330, 3150, 1640, 1510
NMR (DMSO-d6) δ (ppm): 9.55, 9.07, 7.50–6.50, 6.00, 3.20–2.80, 1.10

EXAMPLE 51

2-[Bis(4-hydroxyphenyl)methyl]-N-methyl-N-phenylbenzamide (Compound 53)

Melting point 246 –247° C.
IR (KBr) cm$^{-1}$: 3400, 3150, 1615, 1585, 1515, 1490
NMR (DMSO-d$_6$) δ (ppm): 9.10, 7.40–6.40, 5.70, 3.25

EXAMPLE 52

N-Cyclopropyl-2-[bis(4-hydroxyphenyl)methyl]benzamide (Compound 54)

Melting point: 221 –226° C.
IR (KBr) cm$^{-1}$: 3380, 1895, 1725, 1632, 1610, 1594, 1510, 1503, 1479, 1445, 1361, 1309, 1227, 1172, 1105, 1045, 956, 814, 778, 754, 672, 625, 579, 562, 516
NMR (DMSO-d6) δ (ppm): 9.14, 8.05, 7.30, 7.22, 6.96, 6.80, 6.64, 5.88, 2.7–2.6, 0.60–0.53, 0.33–0.27

EXAMPLE 53

1-{2-[Bis(4-hydroxyphenyl)methyl]benzoyl}-4-methylpiperazine (Compound 55)

Melting point: 226 –231° C.
IR (KBr) cm$^{-1}$: 3150, 1737, 1605, 1587, 1512, 1466, 1439, 1365, 1269, 1250, 1171, 1137, 1099, 1046, 1022, 994, 848, 822, 777, 745, 650, 579, 562, 516
NMR (DMSO-d$_6$) δ (ppm): 9.24, 9.20, 7.31, 7.23, 7.14, 6.98, 6.79, 6.69, 6.67, 5.57, 3.51, 3.29, 3.0–2.8, 2.5–2.3, 2.3–2.1, 2.11

EXAMPLE 54

4-{2-[Bis(4-hydroxyphenyl)methyl]benzoyl}piperidone (Compound 56)

NMR (DMSO-d$_6$) δ (ppm): 9.23, 7.27, 6.82, 7.1–6.7, 6.67, 5.62, 3.9–3.6, 2.9–2.1

EXAMPLE 55

2-[Bis(4-hydroxyphenyl)methyl]-N-(N',N'-dimethyl-2-aminoethyl)benzamide hydrochloride (Compound 57)

Melting point: 215 –219° C.
IR (KBr) cm$^{-1}$: 3178, 1631, 1612, 1594, 1552, 1510, 1479, 1442, 1361, 1319, 1262, 1225, 1168, 1104, 1021, 987, 847, 818, 788, 745, 666, 582
NMR (DMSO-d6) δ (ppm): 10.45, 9.24, 8.35, 7.5–7.2, 6.95, 6.80, 6.67, 5.98, 3.43, 2.93, 2.72

EXAMPLE 56

1-{2-[Bis(4-hydroxyphenyl)methyl]benzoyl}-1,2,3,6-tetrahydropyridine (Compound 58)

Melting point: 227 –230° C.
IR (KBr) cm$^{-1}$: 3330, 1602, 1579, 1512, 1445, 1366, 1238, 1172, 1100, 1046, 818, 774, 749, 655, 635, 576, 561, 515
NMR (DMSO-d6) δ (ppm): 9.2, 9.1, 7.4,–7.2, 7.2–7.1, 7.00, 6.81, 6.67, 5.68, 5.49, 4.3–4.2, 3.7–3.6, 3.0–2.8, 2.4–2.2, 2.1–2.0, 2.0–1.8

EXAMPLE 57

N-(2-Ethoxyethyl)-2-[bis(4-hydroxyphenyl)methyl]benzamide (Compound 59)

Melting point: 233 –235° C.
IR (KBr) cm$^{-1}$: 3320, 1990, 1610, 1590, 1560, 1504, 1481, 1443, 1367, 1347, 1315, 1259, 1221, 1170, 1120, 954, 864, 847, 818, 740, 715, 675, 624, 564, 508
NMR (DMSO-d$_6$) δ (ppm): 9.15, 8.00, 7.4–7.1, 7.24, 7.1–6.9, 6.82, 6.65, 5.90, 3.38, 3.32, 1.07

EXAMPLE 58

N-(exo-Bicyclo[2.2.1]hept-2-yl)-2-[bis(4-hydroxyphenyl)benzamide (Compound 60)

Melting point: 179 –181° C.
IR (KBr) cm$^{-1}$: 3370, 2946, 1630, 1610, 1592, 1512, 1445, 1241, 1173, 1104, 810, 750
NMR (DMSO-d$_6$) δ (ppm) 9.14, 7.80, 7.22, 7.3–7.1, 7.0–6.8, 6.80, 6.65, 5.85, 3.6–3.4, 2.2–1.9, 1.6–0.8

EXAMPLE 59

N-(2,2,2-Trifluoroethyl)-2-[bis(4-hydroxyphenyl)methyl]benzamide (Compound 61)

Melting point: 165 –166° C.
IR (KBr) cm$^{-1}$: 3525, 3345, 1892, 1650, 1612, 1598, 1540, 1511, 1446, 1392, 1314, 1253, 1175, 961, 826, 766, 665, 577, 562
NMR (DMSO-d$_6$) δ (ppm): 9.16, 8.83, 7.4–7.1, 7.1–6.9, 6.82, 6.65, 5.81, 4.1–3.7

EXAMPLE 60

2-[Bis(4-hydroxyphenyl)methyl]-N-(4-propylphenyl)benzamide (Compound 62)

Melting point: 218 –219° C.
IR (KBr) cm$^{-1}$: 3310, 1594, 1512, 1445, 1411, 1327, 1236, 1170, 1104, 835, 821, 744, 665, 562
NMR (DMSO-d$_6$) δ (ppm): 10.06, 9.14, 7.6–7.1, 7.1–6.9, 6.82, 6.63, 5.87, 2.47, 1.54, 0.85

EXAMPLE 61

2-[Bis(4-hydroxyphenyl)methyl]-N-(5-indanyl)benzamide (Compound 63)

Melting point: 220 –223° C.

IR (KBr) cm$^{-1}$: 3300, 2950, 2840, 1895, 1650, 1593, 1513, 1438, 1334, 1220, 1172, 1105, 1076, 1044, 1014, 946, 901, 865, 818, 746, 674, 625, 578, 561, 519

NMR (DMSO-d$_6$) δ (ppm): 10.04, 9.17, 7.6–7.2, 7.2–6.9, 6.83, 6.65, 5.88, 3.0–2.6, 2.3–1.8

EXAMPLE 62

2-[Bis(4-hydroxyphenyl)methyl]-N-(4-morpholinophenyl)benzamide (Compound 64)

Melting point: 151–155° C.

IR (KBr) cm$^{-1}$: 3300, 1615, 1596, 1514, 1447, 1413, 1382, 1321, 1233, 1172, 1110, 1047, 927, 902, 816, 740

NMR (DMSO-d$_6$) δ (ppm): 9.94, 9.16, 7.6–7.2, 7.2–6.9, 6.84, 6.65, 5.90, 3.8–3.6, 3.2–2.9

EXAMPLE 63

N-[2-(3-Chloro-5-pyridyloxy)pyridin-5-yl]-2-[bis(4-hydroxyphenyl)methyl]benzamide (Compound 65)

Melting point: 122–125° C. (decomposed at 122° C.)

IR (KBr) cm$^{-1}$: 3230, 1642, 1610, 1509, 1478, 1429, 1380, 1226, 1172, 1103, 1018, 933, 819

NMR (DMSO-d$_6$) δ (ppm): 10.33, 9.16, 8.48, 8.44, 8.31, 8.10, 7.87, 7.5–7.3, 7.15, 7.04, 6.83, 6.65, 5.89

EXAMPLE 64

1-{2-[Bis(4-hydroxyphenyl)methyl]benzoyl}-4-phenylpiperazine (Compound 66)

NMR (DMSO-d$_6$) δ (ppm): 9.21, 9.19, 7.36–7.15, 7.00, 6.84–6.63, 5.59, 3.64, 3.28, 3.18–2.95, 2.73, 2.54, 2.23

EXAMPLE 65

N-(tert-Butyl)-2-[bis(4-hydroxyphenyl)methyl]benzamide (Compound 67)

Melting point: 264–266° C.

IR (KBr) cm$^{-1}$: 3400, 3330, 1630, 1620, 1595, 1550, 1510, 1460, 1260, 1240

NMR (DMSO-d$_6$) δ (ppm): 9.10, 7.40, 7.35–6.50, 5.85, 1.26

EXAMPLE 66

2-[Bis(4-hydroxyphenyl)methyl]-N-(2-methylphenyl)benzamide (Compound 68)

Melting point: 267–269° C.

IR (KBr) cm$^{-1}$: 3330, 1660, 1620, 1600, 1590, 1535, 1520, 1460, 1320

NMR (DMSO-d$_6$) δ (ppm): 9.45, 9.05, 7.55–6.45, 5.95, 2.10

EXAMPLE 67

N-(4-Butoxyphenyl)-2-[bis(4-hydroxyphenyl)methyl]benzamide (Compound 69)

Melting point: 110–112° C.

IR (KBr) cm$^{-1}$: 3530, 3300, 2960, 1635, 1610, 1600, 1530, 1525, 1245

NMR (DMSO-d$_6$) δ (ppm): 9.95, 9.10, 7.65–7.20, 7.15–6.35, 5.90, 4.05–3.80, 1.90–0.90

EXAMPLE 68

2-[Bis(4-hydroxyphenyl)methyl]-N,N-diphenylbenzamide (Compound 70)

Melting point 262–263° C.

IR (KBr) cm$^{-1}$: 3330, 3180, 1630, 1618, 1595, 1520, 1495, 1450, 1380, 1360, 1245, 1220

NMR (DMSO-d$_6$) δ (ppm): 9.13, 7.40–6.45, 5.90

EXAMPLE 69

3-{2-[Bis(4-hydroxyphenyl)methyl]benzoyl}-3-azabicyclo[3.2.2]nonane (Compound 71)

Melting point: 164–166° C.

IR (KBr) cm$^{-1}$: 3350, 2930, 2860, 1610, 1590, 1520, 1460, 1230

NMR (DMSO-d$_6$) δ (ppm): 9.05, 7.30–6.40, 5.40, 4.25–3.90, 2.55–1.90, 1.85–1.10

EXAMPLE 70

2-[Bis(4-hydroxyphenyl)methyl]-N-(2-thenyl)benzamide (Compound 72)

Melting point: 109–111° C.

IR (KBr) cm$^{-1}$: 3540, 3350, 1635, 1620, 1600, 1511, 1450

NMR (DMSO-d$_6$) δ (ppm): 9.05, 8.70, 7.45–6.40, 5.90, 4.48

EXAMPLE 71

N-[(Tricyclo[3.3.1.1$^{3,7}$]dec-1-yl)methyl]-2-[bis(4-hydroxyphenyl)methyl]benzamide (Compound 73)

Melting point: 149–151° C.

IR (KBr) cm$^{-1}$: 3350, 2900, 2850, 1640, 1620, 1530, 1520, 1450, 1230

NMR (DMSO-d$_6$) δ (ppm): 9.00, 7.85, 7.40–6.40, 5.92, 2.85, 2.00–1.10

EXAMPLE 72

2-[Bis(4-hydroxyphenyl)methyl]-N-(2-methylthiophenyl)benzamide (Compound 74)

Melting point: 119–121° C.

IR (KBr) cm$^{-1}$: 3400, 3250, 1660, 1650, 1615, 1600, 1515, 1505, 1440, 1245

NMR (DMSO-d$_6$) δ (ppm): 9.50, 9.10, 7.65–6.35, 6.00, 2.47

EXAMPLE 73

N,N-Dicyclohexyl-2-[bis(4-hydroxyphenyl)methyl]benzamide (Compound 75)

Melting point: >300° C.

IR (KBr) cm$^{-1}$: 3260, 2930, 2850, 1610, 1590, 1520, 1440, 1370, 1240

NMR (DMSO-d$_6$) δ (ppm): 9.10, 7.40–6.35, 5.60, 2.90–2.20, 1.90–0.50

EXAMPLE 74

1-(2-Methoxyphenyl)-4-{2-[bis(4-isopropoxyphenyl)methyl]benzoyl}piperazine (Compound 9)

In 20 ml of dimethylformamide were dissolved 0.72 g of Compound 8 obtained by Example 10 and 3 g of cesium carbonate. To this solution was added 4 ml of isopropyl bromide, and the resulting mixture was stirred at 70° C. for 9 hours. The mixture was concentrated under reduced pressure, and water was added to the residue. The resulting mixture was extracted with chloroform, and the extract was washed with saturated aqueous sodium chloride and then dried over anhydrous sodium sulfate. The solvent was evaporated under reduced pressure, and the residue was recrystallized to obtain 0.75 g of the desired compound (Compound 9).

Melting point: 120.0–121.0° C.

IR (KBr) cm$^{-1}$: 1632, 1504, 1241

NMR (CDCl$_3$) δ (ppm): 7.29–6.71, 5.88, 4.41, 3.81, 3.82–2.25, 1.32–1.21

EXAMPLE 75

1{2-[Bis(4-isopropoxyphenyl)methyl]benzoyl}piperidine (Compound 6)

The desired compound (Compound 6) was obtained in a similar manner as in Example 74, using Compound 5 obtained by Example 9.

Melting point 142.5 –143.5° C.

IR (KBr) cm 1620, 1505, 1433
NMR (CDCl$_3$) δ (ppm): 7.31–6.70, 5.79, 4.48, 1.30

EXAMPLE 76

N-(Tricyclo[3.3.1.1$^{3,7}$]dec-1-yl)-2-[bis(4-methoxymethoxyphenyl)methyl]benzylamine (Compound 76)

In a mixture of 50 ml of saturated aqueous sodium hydrogencarbonate and 50 ml of chloroform was suspended 0.94 g of 1-adamantanamine hydrochloride, and the suspension was then dissolved with stirring. Thereafter, the organic layer was separated, and the aqueous layer was extracted with chloroform. The chloroform layer was combined with the organic layer, dried over anhydrous magnesium sulfate. The solvent was evaporated under reduced pressure. The residue and 1.96 g of 2-[bis(4-methoxymethoxyphenyl)methyl]benzaldehyde obtained by Reference Example 7 were dissolved in 50 ml of ethanol, and the solution was stirred overnight. Then, 0.85 g of sodium borohydride was added thereto, and the mixture was stirred overnight. The reaction mixture was concentrated under reduced pressure, and water was added to the residue. The aqueous mixture was extracted with chloroform, and the organic layer was separated. The aqueous layer was again extracted with chloroform. The organic layer was combined and dried over anhydrous magnesium sulfate. The solvent was evaporated under reduced pressure, and the residue was purified by silica gel column chromatography to afford 2.1 g of the desired compound (Compound 76) as an oily matter.

IR (neat) cm$^{-1}$: 1609, 1507, 1232
NMR (CDCl$_3$) δ (ppm): 7.68, 7.26–6.79, 5.97, 5.14, 3.73, 3.46, 1.98–1.50

EXAMPLE 77

N-(Cyclooctyl)-2-[bis(4-methoxymethoxyphenyl)methyl]benzylamine (Compound 77)

In 50 ml of ethanol was dissolved 0.69 g of cyclooctylamine. To the solution was added 1.96 g of 2-[bis(4-methoxymethoxyphenyl)methyl]benzaldehyde obtained by Reference Example 7, and the mixture was stirred overnight. Then, 0.85 g of sodium borohydride was added thereto, and the reaction mixture was stirred for 2 hours. Thereafter, the solvent was evaporated under reduced pressure, and water was added to the residue. The aqueous mixture was extracted with chloroform, and the organic layer was separated. The aqueous layer was extracted with chloroform, and the organic layer was combined and dried over anhydrous magnesium sulfate. The solvent was evaporated under reduced pressure, and the residue was purified by silica gel chromatography to afford 2.25 g of the desired product (Compound 77) as an oily matter.

IR (neat) cm$^{-1}$: 1609, 1508, 1234

NMR (CDCl$_3$) δ (ppm): 7.30–6.87, 5.95, 5.14, 3.69, 3.46, 2.65, 1.70–1.40

In the following Examples 78 to 81, desired compounds were obtained in a similar manner as in Example 77, except that corresponding amines were used in place of cyclooctylamine.

EXAMPLE 78

N-(1-Indanyl)-2-[bis(4-methoxymethoxyphenyl)methyl]benzylamine (Compound 78)

IR (neat) cm$^{-1}$: 1609, 1510, 1246
NMR (CDCl$_3$) δ (ppm): 7.38–6.87, 6.00, 5.14, 4.17, 3.81, 3.47, 3.01–2.71, 2.45–2.32, 1.85–1.46

EXAMPLE 79

N-Cyclohexyl-2-[bis(4-methoxymethoxyphenyl)methyl]benzylamine (Compound 79)

IR (neat) cm$^{-1}$: 1609, 1508, 1234
NMR (CDCl$_3$) δ (ppm): 7.32–6.87, 5.93, 5.14, 3.72, 3.46, 2.31, 1.71–0.98

EXAMPLE 80

2-[Bis(4-methoxymethoxyphenyl)methyl]-N-[1,2-bis(4'-methoxyphenyl)ethhyl]benzylamine (Compound 80)

IR (neat) cm$^{-1}$: 1610, 1510, 1246
NMR (CDCl$_3$) δ (ppm): 7.20–6.73, 5.67, 5.12, 3.80, 3.73, 3.47, 2.83–2.64

EXAMPLE 81

N-[1-(1,2,3,4-Tetrahydronaphthyl)]-2-[bis(4-methoxymethoxyphenyl)methyl]benzylamine (Compound 81)

IR (neat) cm$^{-1}$: 1608, 1502, 1232
NMR (CDCl$_3$) δ (ppm): 7.24–6.80, 6.00, 5.13, 3.78, 3.47, 2.78–2.65, 1.85–1.75, 1.45–1.40

EXAMPLE 82

2-[Bis(4-benzyloxyphenyl)methyl]-N-(cyclooctyl)benzylamine (Compound 82)

In 50 ml of ethanol was dissolved 3 g of cyclooctylamine. To the solution was added 11.41 g of 2-[bis-(4-benzyloxyphenyl)methyl]benzaldehyde obtained by Reference Example 8, and the mixture was heated under reflux for 2 hours. Thereafter, 1.78 g of sodium borohydride was added thereto, and the mixture was heated under reflux for 2 hours. The solvent was evaporated under reduced pressure, and water was added to the residue. The aqueous mixture was extracted with ether, and the organic layer was separated. The aqueous layer was extracted with ether, and then the organic layers were combined and dried over anhydrous magnesium sulfate. The solvent was evaporated under reduced pressure, and the residue was recrystallized to afford 9.19 g of the desired product (Compound 82).

IR (KBr) cm$^{-1}$: 1606, 1504, 1226
NMR(DMSO-d$_6$) δ (ppm): 7.45–7.28, 7.18–7.14, 6.94, 6.88–6.79, 5.95, 5.05, 3.64, 2.49, 1.63–1.38

EXAMPLE 82

2-[Bis(4-benzyloxyphenyl)methyl]-N-[4-(1-benzylpiperidyl)]benzylamine dihydrochloride (Compound 83)

At first, 14.9 g of 2-[bis(4-benzyloxyphenyl)methyl]-N-[4-(1-benzylpiperidyl)]benzylamine was obtained in a similar manner as in Example 82, except that 4-amino-1-benzylpiperidine was used in place of cyclooctylamine. To the compound was added ethyl acetate saturated with hydrogen chloride, and the mixture was stirred for 10 minutes. Precipitated crystals were collected by filtration and then subjected to recrystallization to afford 8.75 g of the desired compound (Compound 83).

IR (KBr) cm$^{-1}$: 1607, 1511, 1214
NMR(DMSO-d$_6$) δ (ppm): 7.64–7.29, 7.02–6.80, 5.95, 5.05, 4.24, 4.04, 3.41–3.26, 2.95, 2.22–2.11

EXAMPLE 84

N-[4-(1-Benzylpiperidyl)]-2-[bis(4-hydroxyphenyl)methyl]benzylamine (Compound 84)

In 50 ml of methanol was dissolved 0.95 g of 4-amino-1-benzylpiperidine. To the solution was added 1.95 g of 2-[bis(4-methoxymethoxyphenyl)methyl]benzaldehyde obtained by Reference Example 7, and the mixture was stirred overnight. Then, 0.85 g of sodium borohydride was added thereto, and the mixture was stirred overnight. The solvent was evaporated under reduced pressure, and water was added to the residue. The aqueous mixture was extracted with ethyl acetate, and the organic layer was separated. The aqueous layer was extracted with ethyl acetate, and the organic layers were combined and dried over anhydrous magnesium sulfate. The solvent was evaporated under reduced pressure, and 30 ml of 2N aqueous hydrochloric acid and 30 ml of methanol were added to the residue. The mixture was stirred for 7 hours at room temperature, and the mixture was neutralized with a saturated aqueous sodium hydrogencarbonate. Thereafter, water was added thereto, and precipitates were collected by filtration, recrystallized from a mixture of water and ethanol and then decolored with activated carbon to afford 1.65 g of the desired compound (Compound 84)

Melting point: 127.8–127.9° C.
IR (KBr) cm$^{-1}$: 1612, 1510, 1252
NMR (CDCl$_3$) δ (ppm): 9.2, 7.32–7.11, 6.82–6.64, 5.81, 3.61, 3.42–3.25, 2.7214 2.66, 2.50–2.31, 1.96–1.86, 1.68–1.62, 1.24–1.21

EXAMPLE 85

N-Cyclooctyl-2-[bis(4-hydroxyphenyl)methyl]benzylamine (Compound 85)

Two grams of 2-[bis(4-benzyloxyphenyl)methyl]-N-(cyclooctyl)benzylamine obtained by Example 82 was dissolved in 120 ml of a mixture of ice-cooled hydrogen bromide-acetic acid solution. The solution was stirred for 2 hours, and the mixture was added to a mixture of ice and a saturated aqueous sodium hydrogencarbonate, stirred and then neutralized with sodium hydrogencarbonate. Thereafter, it was extracted with ethyl acetate, washed with water and dried over anhydrous magnesium sulfate. The solvent was evaporated under reduced pressure, and the residue was subjected to recrystallization to afford 0.76 g of the desired compound (Compound 85).

IR (KBr) cm$^{-1}$: 1612, 1508, 1220
NMR(DMSO-d$_6$) δ (ppm): 9.25, 7.49–7.45, 7.30–7.27, 6.89–6.68, 5.68, 3.96, 1.96–1.41

EXAMPLE 86

N-(Tricyclo[3.3.1.1$^{3,7}$]dec-2-yl)-2-[bis(4-hydroxyphenyl)methyl]benzylamine hydrochloride (Compound 86)

At first, 4.2 g of N-(2-adamantyl)-2-[bis(4-methoxymethoxyphenyl)methyl]benzylamine was obtained in a similar manner as in Example 76, except that 2-adamantanamine hydrochloride was used in place of 1-adamantanamine hydrochloride. To the compound was added a mixture of isopropyl alcohol and ethyl acetate saturated with hydrogen chloride, and the mixture was stirred for 30 minutes. Thereafter, ether was added to the reaction mixture, and precipitates were collected by filtration and then dried to afford 1.24 g of the desired compound (Compound 86).

IR (KBr) cm$^{-1}$: 1725, 1613, 1511
NMR(DMSO-d$_6$) δ (ppm): 9.:30, 9.09, 7.72, 7.31, 6.85–6.68, 5.68, 4.07, 3.08, 2.16–2.04, 1.80–1.49

EXAMPLE 87

2-[Bis((hydroxyphenyl)methyl]-N-(diphenylmethyl)-benzylamine hydrochloride (Compound 87)

At first, 4.88 g of 2-[bis(methoxymethoxyphenyl)-methyl-N-(diphenylmethyl)benzylamine was obtained in a similar manner as in Example 77, except that aminodiphenylmethane was used in place of cyclooctylamine. The compound was then dissolved in ethyl acetate saturated with hydrochloric acid. The mixture was stirred for 10 minutes, and then ether was added to the mixture. Precipitates were collected by filtration and then dried to afford 1.3 g of the desired compound of hydrochloride (Compound 87).

IR (KBr) cm$^{-1}$: 1612, 1512, 1224
NMR (DMSO-d$_6$) δ (ppm): 10.21, 9.19, 7.73–7.29, 6.80–6.54, 5.62, 5.02, 4.76, 3.88, 3.50

EXAMPLE 88

1-[2-Bis(4-benzyloxyphenyl)methylphenyl]-N-(1-benzylpiperidin-4-yl)pentylamine dihydrochloride (Compound 88)

In 30 ml of toluene were dissolved 4 g of N-[2-bis(4-benzyloxyphenyl)methylbenzylidene]-(1-benzylpiperidin-4-yl)amine obtained by Reference Example 9 and the solution was cooled to 0° C. To the solution was dropwise added 5 ml of 1.4 M n-butyl lithium/hexane solution, and the mixture was stirred for 2 hours The reaction was terminated by the addition of saturated aqueous ammonium chloride. The reaction mixture was extracted with ethyl acetate, and the organic layer was dried over anhydrous magnesium sulfate. The solvent was evaporated under reduce pressure to afford crude product. The crude product was purified by silica gel column chromatography, and the purified product was converted into dihydrochloride by adding ethyl acetate saturated with hydrochloric acid. The solvent was evaporated under reduced pressure, and the residue was washed with either to afford 2.5 g of the desired compound (Compound 88).

Melting point: 147–150° C.
IR (KBr) cm$^{-1}$: 3400, 1606, 1580, 1505, 1453, 1379, 1225, 1175, 1110, 1012, 803, 738, 696
NMR (DMSO-d$_6$) δ (ppm): 8.1–6.7, 5.69, 5.01, 4.3–4.0, 3.30, 2.3–1.8, 1.3–0.6

EXAMPLE 89

1-(2-Chlorophenyl)-4-{2-[bis(4-hydroxyphenyl)methyl]benzyl}piperazine (Compound 89)

In 50 ml of tetrahydrofuran were dissolved 1.5 g of 1-(2-chlorophenyl)piperazine and 5 ml of triethylamine, and 3.4 g of 2-[bis(4-hydroxyphenyl)methyl]benzylbromide was added thereto. The mixture was heated under reflux for 3.5 hours, and then insoluble substances were filtered off. The filtrate was concentrated, and the residue was subjected to extraction with the addition of water and ethyl acetate. The organic layer was separated, and the aqueous layer was then extracted with ethyl acetate. The organic layers were combined and then dried over anhydrous magnesium sulfate. The solvent was evaporated off under reduced pressure, and the residue was purified by silica gel chromatography to afford 0.54 g of the desired compound (Compound 89).

Melting point: 149-151° C.
IR (KBr) cm$^{-1}$: 3375, 1610, 1510
NMR (DMSO-d$_6$) δ (ppm): 9.15, 7.39, 7.28-7.02, 6.88-6.66, 6.08, 3.41, 2.93, 2.50

In the following Examples 90 to 99, the desired compounds were obtained in a similar manner as in Example 89, except that a corresponding amine was used in place of 1-(2-chlorophenyl)piperazine.

EXAMPLE 90

1-{2-[Bis(4-hydroxyphenyl)methyl]benzyl}-4-(3-methoxyphenyl)piperazine (Compound 90)

Melting point: 128 -130° C.
IR (KBr) cm$^{-1}$: 3375, 1612, 1510
NMR (DMSO-d$_6$) δ (ppm): 9.16, 7.23-7.16, 6.92-6.65, 6.10, 3.76, 3.39, 2.93, 2.50

EXAMPLE 91

1-{2-[Bis(4-hydroxyphenyl)methyl]benzyl}-1,2,3,4-tetrahydroquinoline (Compound 91)

Melting point: 160 -163° C.
IR (KBr) cm$^{-1}$: 3375, 1600, 1510
NMR (DMSO-d$_6$) δ (ppm): 9.20, 7.13-7.06, 6.87-6.65, 6.39, 5.79, 5.57, 4.33, 3.24, 2.70, 1.89

EXAMPLE 92

1-{2-[Bis(4-hydroxyphenyl)methyl]benzyl}-4-(2-methoxyphenyl)piperazine (Compound 92)

Melting point: 175 -178° C.
IR (KBr) cm$^{-1}$: 3375, 1612, 1510
NMR (DMSO-d$_6$) δ (ppm): 9.15, 7.23-7.16, 6.92-6.65, 6.09, 3.79, 3.39, 2.93, 2.50

EXAMPLE 93

1-{2-[Bis(4-hydroxyphenyl)methyl]benzyl}-4-(2-oxo-3oxazolizyl)piperidine hydrochloride (Compound 93)

Melting point: 213 -216° C.
IR (KBr) cm$^{-1}$: 3225, 1709, 1511
NMR (DMSO-d$_6$) δ (ppm): 9.30, 7.88, 7.36-7.26, 6.95-6.68, 5.87, 4.27, 4.15, 3.82, 3.51-3.19, 2.20, 1.82

EXAMPLE 94

1-[2-(Trifluoromethyl)phenyl]-4-{2-[bis(4-hydroxyphenyl)methyl]benzyl}piperazine hydrochloride (Compound 94)

Melting point: 208 -210° C.
NMR (DMSO-d$_6$) δ (ppm): 11.35, 7.91, 7.48, 7.38-7.13, 6.91-6.68, 6.00, 4.76, 3.94, 3.89, 3.58-3.26

EXAMPLE 95

2-{2-[Bis(4-hydroxyphenyl)methyl]benzyl}-1,2,3,4-tetrahydroisoquinoline (Compound 95)

Melting point: 248 -250° C.
NMR (DMSO-d$_6$) δ (ppm): 9.30, 7.88, 7.36-7.26, 6.95-6.67, 5.94, 4.30-4.18, 3.09-2.73, 2.28-1.10

EXAMPLE 96

1-{2-[Bis(4-hydroxyphenyl)methyl]benzyl}-4-piperidinopiperidine hydrochloride (Compound 96)

Melting point: 290 -293° C.
IR (KBr) cm$^{-1}$: 3375, 1611, 1511
NMR (DMSO-d$_6$) δ (ppm): 9.31, 7.80, 7.36-7.23, 6.89-6.62, 5.90, 4.15, 3.37-2.90, 2.30-1.43

EXAMPLE 97

1-{2-[Bis(4-hydroxyphenyl)methyl]benzyl}-5,6,11,12-tetrahydrodibenz[b,f]azocine hydrochloride (Compound 97)

Melting point: 175 -177° C.
IR (KBr) cm$^{-1}$: 3210, 1612, 1511
NMR (DMSO-d$_6$) δ (ppm): 7.38-6.61, 5.80, 4.24-4.11, 3.16-3.10

EXAMPLE 98

1-(4-Acetylphenyl)-4-{2-[bis(4-hydroxyphenyl)methyl]benzyl}piperazine (Compound 98)

NMR (DMSO-d$_6$) δ (ppm): 9.17, 7.80, 7.26-6.81, 6.66, 6.07, 3.41, 3.37-3.30, 2.44

Example 99

1-{2-[Bis(4-hydroxyphenyl)methyl]benzyl}-4-(2-pyridyl)piperazine (Compound 99)

IR (KBr) cm$^{-1}$: 3215, 1608, 1511
NMR (DMSO-d$_6$) δ (ppm): 9.18, 8.10, 7.52, 7.20, 6.90-6.65, 6.08, 3.41-3.25, 2.51-2.41

EXAMPLE 100

N-{2-[Bis(4-acetoxyphenyl)methyl]phenyl}-3,4-dimethoxybenzamide (Compound 100)

In 50 ml of tetrahydrofuran were dissolved 1.26 g of 4,4'-diacetoxy-2''-aminotriphenylmethane obtained by Reference Example 11 and 0.4 ml of triethylamine, and the solution was cooled with ice. Subsequently, a solution of 0.6 g of 3,4-dimethoxybenzoyl chloride in 20 ml of tetrahydrofuran was added thereto under ice cooling, and the temperature of the mixture was raised gradually to room temperature. The mixture was stirred for 2 hours, and concentrated. The concentrate was subjected to extraction with water and ethyl acetate. The organic layer was separated, and the aqueous layer was extracted with ethyl acetate. The organic layers were combined, washed with water and then dried over anhydrous magnesium sulfate. The solvent was evaporated under reduced pressure, and the residue was recrystallized to afford 1.58 g of the desired compound (Compound 100).

NMR (CDCl$_3$) δ (ppm): 7.92-7.85, 7.41-6.55, 5.60, 3.92, 3.87, 2.30

EXAMPLE 101

N-{2-[Bis(4-acetoxyphenyl)methyl]phenyl}cyclohexanecarboxamide (Compound 101)

In 30 ml of pyridine was dissolved 1.5 g of 4,4'-diacetoxy-2''-aminotriphenylmethane obtained by Reference Example 11, and then 0.59 g of cyclohexanecarbonyl chloride was added thereto under ice cooling. The temperature of the mixture was raised to room temperature, and the mixture was stirred for 2 hours, and then concentrated under reduced pressure. The residue was subjected to extraction with water and chloroform. The organic layer was separated, and the aqueous layer was extracted with chloroform. The organic layers were combined and then washed with 2N hydrochloric acid, saturated aqueous sodium hydrogencarbonate and saturated aqueous sodium chloride, in order. The layer was dried over anhydrous magnesium sulfate, and the solvent was evaporated under reduced pressure to afford 2.21 g of Compound 101.

NMR (CDCl$_3$) δ (ppm): 7.75–7.60, 7.25–6.50, 5.52, 2.45–2.35, 2.20, 2.00–1.05

In the following Example 102–116, the desired compound was obtained in a similar manner as in Example 101, except that a corresponding acid chloride was used in place of cyclohexanecarbonyl chloride.

EXAMPLE 102

N-{2-[Bis(4-acetoxyphenyl)methyl]phenyl}-4-nitrobenzamide (Compound 102)

NMR (CDCl ) δ (ppm): 8.25–8.05, 8.00–7.80, 7.55–6.55, 5.50, 2.30

EXAMPLE 103

N-{2-[Bis(4-acetoxyphenyl)methyl]phenyl}-4,7,7-trimethyl3-oxo-2-oxabicyclo[2.2.1]heptanecarboxamide (Compound 103)

NMR (CDCl$_3$) δ (ppm): 8.05–7.80, 7.40–6.50, 5.50, 2.60–1.60, 1.05, 0.70

EXAMPLE 104

N-{2-[Bis(4-acetoxyphenyl)methyl]phenyl}-2-methoxybenzamide (Compound 104)

NMR (CDCl$_3$) δ (ppm): 9.15, 8.20, 7.75, 7.50–6.55, 5.70, 3.45, 2.25

EXAMPLE 105

N-{2-[Bis(4-acetoxyphenyl)methyl]phenyl}-3-methoxybenzamide (Compound 105)

NMR (CDCl$_3$) δ (ppm): 8.00–7.80, 7.55–6.50, 5.60, 3.80, 2.30

EXAMPLE 106

N-{2-[Bis(4-acetoxyphenyl)methyl]phenyl}-1-naphthalenecarboxamide (Compound 106)

NMR (CDCl$_3$) δ (ppm): 8.40–8.15, 8.05–7.60, 7.60–6.55, 5.62, 2.25

EXAMPLE 107

N-{2-[Bis(4-acetoxyphenyl)methyl]phenyl}-3-pyridinecarboxamide (Compound 107)

NMR (CDCl$_3$) δ (ppm): 8.75–8.50, 7.85–7.45, 7.35–6.65, 5.60, 2.25

EXAMPLE 108

N-{2-[Bis(4-acetoxyphenyl)methyl]phenyl}tricyclo[3.3.1.0$^{3,7}$]-nonane-3-carboxamide (Compound 108)

NMR (CDCl ) δ (ppm): 8.00, 7.40–6.60, 5.50, 2.25, 2.10–1.30

EXAMPLE 109

N-{2-[Bis(4-acetoxyphenyl)methyl]phenyl}-(3-methyltricyclo[3.3.1.1$^{3,7}$]dec-1-yl)acetamide (Compound 109)

NMR (CDCl$_3$) δ (ppm): 7.85, 7.30–6.55, 5.53, 2.27, 2.15–1.75, 1.65–1.05, 0.78

EXAMPLE 110

N-{2-[Bis(4-acetoxyphenyl)methyl]phenyl}bicyclo[2.2.1]hept-2-yl-acetamide (Compound 110)

NMR (CDCl$_3$) δ (ppm): 7.75–7.60, 7.30–6.55, 5.55, 2.27, 2.10–1.85, 1.55–0.85

EXAMPLE 111

N-{2-[Bis(4-acetoxyphenyl)methyl]phenyl}cinnamide (Compound 111)

NMR (CDCl$_3$) δ (ppm): 7.75–7.55, 7.45–6.55, 6.33, 6.16, 5.63, 2.23

EXAMPLE 112

N-{2-[Bis(4-acetoxyphenyl)methyl]phenyl}-2,2-dimethylpropaneamide (Compound 112)

NMR (CDCl$_3$) δ (ppm): 7.75, 7.30–6.60, 5.47, 2.25, 1.07

EXAMPLE 113

N-{2-[Bis(4-acetoxyphenyl)methyl]phenyl}-4-methoxycarbonylbenzamide (Compound 113)

NMR (CDCl$_3$) δ (ppm): 8.05–7.80, 7.45–7.15, 7.05, 6.85–6.70, 5.50, 3.91, 2.30

EXAMPLE 114

N-{2-[Bis(4-acetoxyphenyl)methyl]phenyl}-3-methoxy-4-nitrobenzamide (Compound 114)

NMR (CDCl$_3$) δ (ppm): 7.95–7.65, 7.55–7.40, 7.35–6.70, 6.50, 5.53, 3.93, 2.30

EXAMPLE 115

N-{2-[Bis(4-acetoxyphenyl)methyl]phenyl}-2-thiophenecarboxamide (Compound 115)

NMR (CDCl$_3$) δ (ppm): 7.85, 7.50–6.65, 5.60, 2.27

EXAMPLE 116

N-{2-[Bis(4-acetoxyphenyl)methyl]phenyl}-4-methoxybenzamide (Compound 116)

NMR (CDCl$_3$) δ (ppm): 7.90, 7.40–6.70, 5.55, 3.80, 2.27

EXAMPLE 117

N-{2-[Bis(4-hydroxyphenyl)methyl]phenyl}-4-nitrobenzamide (Compound 117)

In 30 ml of pyridine was dissolved 1.5 g of 4,4'-diacetoxy-2''-aminotriphenylmethane obtained by Reference Example 11, and then 0.74 g of p-nitrobenzoyl chloride was added thereto under ice cooling. The temperature of the mixture was raised to room temperature, and the mixture was stirred for 2 hours. The solvent was evaporated under reduced pressure. The residue was subjected to extraction with water and chloroform. The organic layer was separated, and the aqueous layer was extracted with chloroform. The organic layers were combined and then washed with 2N hydrochloric acid, saturated aqueous sodium hydrogencarbonate and saturated aqueous sodium chloride in order. The layer was dried over anhydrous magnesium sulfate, and the solvent was evaporated. The residue was dissolved in ethanol. To the solution was added 50 ml of saturated aqueous sodium hydrogencarbonate, and the mixture was heated under reflux for 2 hours. After the reaction was completed, the solvent was evaporated under reduced pressure. Precipitates were washed with water and then recrystallized to afford 1.02 g of the desired compound (Compound 117).

Melting point: 258 -259° C.
IR (KBr) cm$^{-1}$: 3495, 1680, 1605, 1520
NMR (DMSO-d$_6$) δ (ppm): 9.98, 9.17, 8.30, 7.95, 7.40, 7.30-7.18, 6.90-6.60, 5.72

In the following Examples 118 and 119, desired compounds were obtained in a similar manner as in Example 117, except that a corresponding acid halide was used in place of p-nitrobenzoyl chloride.

EXAMPLE 118

N-{2-[Bis(4-hydroxyphenyl)methyl]phenyl}diphenylacetamide (Compound 118)

NMR (DMSO-d$_6$) δ (ppm): 9.58 9.16 7.33-7.08, 6.83, 6.68-6.56, 5.55, 5.13

EXAMPLE 119

N-{2-[Bis(4-hydroxyphenyl)methyl]phenyl}tricyclo[3.3.1.1$^{3,7}$]decane-1-carboxamide (Compound 119)

NMR (DMSO-d$_6$) δ (ppm): 9.20, 7.46, 7.18, 7.06, 6.83-6.66, 5.53, 1.96, 1.68-1.58

EXAMPLE 120

N-{2-[Bis(4-hydroxyphenyl)methyl]phenyl}cyclohexanecarboxamide (Compound 120)

To 2.21 g of Compound 101 obtained by Example 101 was added 50 ml of ethanol and 50 ml of saturated aqueous sodium hydrogencarbonate, and the mixture was heated under reflux for 2 hours. After the reaction was completed, the solvent was evaporated under reduced pressure. Precipitated crystals were washed with water and then recrystallized to afford 1.05 g of the desired compound (Compound 120)

Melting point: 220 -223° C.
IR (KBr) cm$^{-1}$: 3310, 2930, 1660, 1515
NMR (DMSO-d$_6$) δ (ppm): 9.25, 8.89, 7.32, 7.20-7.00, 6.90-6.55, 5.67, 2.25-2.10, 1.75-1.55, 1.35-1.05

In the following Examples 121 to 135, desired compounds were obtained in a similar manner as in Example 120, except that Compound 100, 103, 104, 105, 106, 107, 108, 109, 110, 111, 112, 113, 114, 115 or 116 was used in place of Compound 101.

EXAMPLE 121

N-{2-[Bis(4-hydroxyphenyl)methyl]phenyl}-3,4-dimethoxybenzamide (Compound 121)

NMR (DMSO-d$_6$) δ (ppm): 9.40, 9.16, 7.43-7.13, 7.00, 6.87-6.63, 5.70, 3.82, 3.79

N-{2-[Bis(4-hydroxyphenyl)methyl]phenyl}-4,7,7-trimethyl-3-oxo-2-oxabicyclo[2.2.1]heptanecarboxamide (Compound 122)

Melting point: 229 -231° C.
IR (KBr) cm$^{-1}$: 3360, 1790, 1520
NMR (DMSO-d$_6$) δ (ppm): 9.20, 9.00, 7.47, 7.25-7.05, 6.90-6.60, 5.57, 2.40-2.28, 2.05-1.85, 1.80-1.70, 1.65-1.45, 1.01, 0.98, 0.72

EXAMPLE 123

N-{2-[Bis(4-hydroxyphenyl)methyl]phenyl}-2-methoxybenzamide (Compound 123)

Melting point: 258° C.
IR (KBr) cm$^{-1}$: 3320, 1640, 1515
NMR (DMSO-d$_6$) δ (ppm): 9.36, 9.23, 7.85-7.70, 7.50, 7.25, 7.20-7.05, 6.90-6.60, 5.57, 3.67

EXAMPLE 124

N-{2-[Bis(4-hydroxyphenyl)methyl]phenyl}-3-methoxybenzamide (Compound 124)

Melting point: 165 -168° C.
IR (KBr) cm$^{-1}$: 3395, 1665, 1585
NMR (DMSO-d$_6$) δ (ppm): 8.30, 7.45, 7.40-7.05, 6.87, 6.85-6.55, 3.79

EXAMPLE 125

N-{2-[Bis(4-hydroxyphenyl)methyl]phenyl}-1-naphthalenecarboxamide (Compound 125)

IR (KBr) cm$^{-1}$: 3300, 1650, 1620, 1505
NMR (DMSO-d$_6$) δ (ppm): 9.90, 9.18, 8.10-7.85, 7.65-7.15, 6.95-6.50, 5.89

EXAMPLE 126

N-{2-[Bis(4-hydroxyphenyl)methyl]phenyl}-3-pyridinecarboxamide hydrochloride (Compound 126)

Melting point: 176-178° C.
IR (KBr) cm$^{-1}$: 3090, 1675, 1520
NMR (CD3OD) δ (ppm): 8.95, 8.65, 8.12, 7.45-7.20, 6.95-6.60, 5.70

EXAMPLE 127

N-{2-[Bis(4-hydroxyphenyl)methyl]phenyl}tricyclo[3.3.1.0$^{3,7}$]nonane-3-carboxamide (Compound 127)

Melting point: 155 -157° C.
IR (KBr) cm$^{-1}$: 3200, 2940, 1660, 1510
NMR (DMSO-d$_6$) δ (ppm): 9.20, 8.15, 7.47, 7.19, 7.07, 6.90-6.55, 5.57, 2.21, 1.85-1.40

EXAMPLE 128

N-{2-[Bis(4-hydroxyphenyl)methyl]phenyl}-(3-methyltricyclo[3.3.1.1$^{3,7}$]dec-1-yl-acetamide (Compound 128)

Melting point: 111 -113° C. (
IR (KBr) cm$^{-1}$: 3360, 2900, 1515
NMR (DMSO-d$_6$) δ (ppm): 9.15, 8.90, 7.40, 7.12, 7.05, 6.90-6.60, 5.71, 2.05-1.90, 1.70-1.20, 0.75

EXAMPLE 129

N-{2-[Bis(4-hydroxyphenyl)methylphenyl}bicyclo[2.2.1]hept-2-ylacetamide (Compound 129)

Melting point: 125 -127° C.
IR (KBr) cm$^{-1}$: 3370, 2945, 1660, 1615, 1515
NMR (DMSO-d$_6$) δ (ppm): 9.40-8.80, 7.40, 7.15, 7.05, 6.90-6.55, 5.70, 2.20-1.65, 1.50-0.85

EXAMPLE 130

N-{2-[Bis(4-hydroxyphenyl)methyl]phenyl}cinnamide (Compound 130)

Melting point: 256 -259° C.
IR (KBr) cm 3400, 1680, 1620, 1520
NMR (DMSO-d$_6$) δ (ppm): 9.40, 9.15, 7.65-7.35, 7.21, 7.13, 6.90-6.60, 5.76

EXAMPLE 131

N-{2-[Bis(4-hydroxyphenyl)methyl]phenyl}-2,2-dimethylpropaneamide (Compound 131)

Melting point: 259 -262° C.
IR (KBr) cm$^{-1}$: 3330, 1645, 1510

NMR (DMSO-d$_6$) δ (ppm): 9.18, 8.36, 7.36, 7.18, 7.08, 6.90–6.60, 5.65, 1.05

EXAMPLE 132

N-{2[Bis(4-hydroxyphenyl)methyl]phenyl}-4-carboxybenzamide (Compound 132)

Melting point: 280–182° C.
IR (KBr) cm$^{-1}$: 3400, 1695, 1535
NMR (DMSO-d$_6$) δ (ppm): 13.15, 9.72, 9.18, 8.05–7.70, 7.42, 7.30–7.10, 6.90–6.50, 5.72

EXAMPLE 133

N-{2-[Bis(4-hydroxyphenyl)methyl]phenyl}-3-methoxy-4-nitrobenzamide (Compound 133)

Melting point: 129–131° C.
IR (KBr) cm$^{-1}$: 3495, 1620, 1590, 1520
NMR (DMSO-d$_6$) δ (ppm): 9.90, 9.17, 7.92, 7.49–7.15, 6.90–6.55, 5.70, 3.97

EXAMPLE 134

N-{2-[Bis(4-hydroxyphenyl)methyl]phenyl}-2-thiophenecarboxamide (Compound 134)

Melting point: 240–243° C.
IR (KBr) cm$^{-1}$: 3260, 1630, 1515
NMR (DMSO-d$_6$) δ (ppm): 9.55, 9.20, 7.90–7.00, 6.70, 5.70

EXAMPLE 135

N-{2-[Bis(4-hydroxyphenyl)methyl]phenyl}-4-methoxybenzamide (Compound 135)

Melting point: 154–156° C.
IR (KBr) cm$^{-1}$: 3420, 1605, 1505, 1300
NMR (DMSO-d$_6$) δ (ppm): 9.37, 9.17, 7.70, 7.45, 7.30–7.10, 7.00, 6.90–6.60, 5.72, 3.82

EXAMPLE 136

N-{2-[Bis(4-hydroxyphenyl)methyl]phenyl}-4-aminobenzamide (Compound 136)

In 50 ml of methanol were suspended 1.48 g of Compound 117 obtained by Example 117 and 0.23 g of 10% palladium-carbon, and the suspension was stirred under hydrogen atmosphere at room temperature for 2 hours. After the reaction was completed, the reaction mixture was filtered by using a filter aid. The solvent was evaporated under reduced pressure to afford 0.53 g of the desired compound (Compound 136).

Melting point: 158–161° C.
IR (KBr) cm$^{-1}$: 3400, 1605, 1505
NMR (DMSO-d$_6$) δ (ppm): 9.40–8.90, 8.85, 7.60–7.35, 7 30–7.05, 6.95–6.50, 5.75–5.50

EXAMPLE 137

N-{2-[Bis(4-methoxymethoxyphenyl)methyl]phenyl}-N-methylcyclohexanecarboxamide (Compound 137)

In 50 ml of pyridine were dissolved 2.38 g of 4,4'-dimethoxymethoxy-2''-aminotriphenylmethane obtained by Reference Example 13 and 0.92 g of cyclohexanecarbonyl chloride, and the solution was stirred under ice cooling for 1 hour. The solvent was evaporated under reduced pressure, and the residue was subjected to extraction with ethyl acetate and water. The organic layer was separated, and the aqueous layer was extracted with ethyl acetate. The organic layers were combined and washed with 2N hydrochloric acid, saturated aqueous sodium hydrogencarbonate and saturated sodium chloride, in order. The organic layer was dried over anhydrous magnesium sulfate, and the solvent was evaporated under reduced pressure.

The residue and 0.4 g of sodium hydride were dissolved under ice cooling in 50 ml of N,N-dimethylformamide, and then 0.62 ml of iodomethane was added thereto. The mixture was stirred for 1 hour, and the temperature of the reaction mixture was raised to room temperature and the mixture was stirred for 3.5 hours. Thereafter, the solvent was evaporated under reduced pressure, and the residue was subjected to extraction with water and ether. The organic layer was separated, and the aqueous layer was extracted with ether. The organic layers were combined, washed with saturated aqueous sodium chloride, and then dried over anhydrous magnesium sulfate. The solvent was evaporated under reduced pressure, and the residue was purified by silica gel column chromatography to afford 2.18 g of the desired compound (Compound 137)

NMR (DMSO-d$_6$) δ (ppm): 7.45–6.75, 5.50, 5.10, 3.45, 2.95, 2.20–0.80

EXAMPLE 138

N-{2-[Bis(4-hydroxyphenyl)methyl]phenyl}-N-methylcyclohexanecarboxamide (Compound 138)

In 50 ml of ethyl acetate saturated with hydrogen chloride was dissolved 2.18 g of compound 137 obtained by Example 137, and the solution was stirred for 1 hour. Thereafter, the solvent was evaporated under reduced pressure, and the residue was recrystallized from methanol to afford 0.31 g of the desired compound (Compound 138).

Melting point: 250–252° C.
IR (KBr) cm$^{-1}$: 3410, 3190, 2930, 1630, 1515
NMR (DMSO-d$_6$) δ (ppm): 9.20, 7.40–7.15, 7.05, 6.85–6.60, 5.32, 2.88, 1.85–0.60

Reference Example 1

2-[Bis(4-acetoxyphenyl)methyl]benzoic acid

In 125 ml of pyridine was dissolved 10.15 g of phenolphthalin, and 50 ml of acetic anhydride was added dropwise to the solution at room temperature. The mixture was stirred for 1 hour, and concentrated under reduced pressure, and water was added to the residue. The aqueous mixture was extracted with chloroform, and the chloroform layer was separated, washed with saturated aqueous sodium chloride and then dried over anhydrous magnesium chloride. The solvent was evaporated under reduced pressure to afford 15.78 g of the desired compound as a solid matter.

NMR (CDCl$_3$) δ (ppm): 7.92–7.82, 7.48–6.90, 6.57, 2.27

Reference Example 2

2-[Bis(4-acetoxyphenyl)methyl]benzoyl chloride

In 50 ml of methylene chloride was dissolved 7 g of 2-[bis(4-acetoxyphenyl)methyl]benzoic acid obtained by Reference Example 1, and then 10 ml of thionyl chloride was added dropwise to the solution at room temperature. The reaction mixture was stirred for 2 hours, and the reaction mixture was concentrated under reduced pressure to afford 11.33 g of the desired compound as an oily matter.

IR (neat) cm$^{-1}$: 1758, 1504, 1200
NMR (CDCl ) δ (ppm): 8.24–8.14, 7.53–7.02, 6.32, 2.27

Reference Example 3

Methoxymethyl 2-[bis(4-methoxymethoxyphenyl)methyl]benzoate

In 500 ml of dichloromethane were dissolved 50 g of phenolphthalin and 240 ml of N,N-diisopropylethylamine, and the solution was ice cooled. Subsequently, 59 ml of chloromethyl methyl ether was added dropwise to the solution, and the mixture was heated under reflux for 4 days. The mixture was cooled to room temperature, water was added thereto, and the organic layer was separated. The aqueous layer was extracted with chloroform, and the organic layers were combined, washed with an aqueous 10% citric acid solution and then dried over anhydrous magnesium sulfate. The solvent was evaporated under reduced pressure to afford 77.31 g of the desired compound as an oily matter.

NMR (CDCl$_3$) δ (ppm): 7.87–7.76, 7.45–6.88, 7.47, 5.24, 5.08, 3.41, 3.29

Reference Example 4

Benzyl 2-[bis(4-benzyloxyphenyl)methyl]benzoate

In 500 ml of methyl ethyl ketone were dissolved 50 g of phenolphthalin and 75 g of anhydrous potassium carbonate, and the solution was ice cooled. Subsequently, 58 ml of benzyl bromide was added dropwise to the solution, and the mixture was heated under reflux for 24 hours. The temperature of the mixture was brought back to room temperature, and concentrated. Thereafter, water was added to the residue, and the aqueous mixture was extracted with ethyl acetate. The organic layer was separated, and the aqueous layer was extracted with ethyl acetate. ]he organic layers were combined, washed with an aqueous 10% citric acid and then dried over anhydrous magnesium sulfate. The solvent was evaporated to give 114.61 g of the desired product.

NMR (CDCl$_3$) δ (ppm): 7.8 73, 7.40–7.20, 7.73–7.02, 7.43, 5.12–4.96

Reference Example 5

2-[Bis(4-methoxymethoxyphenyl)methyl]benzyl alcohol

In 500 ml of tetrahydrofuran was dissolved 74 g of methoxymethyl 2-[bis(4-methoxymethoxyphenyl)methyl]benzoate obtained by Reference Example 3. The solution was ice-cooled, 10 g of lithium aluminum hydride was added thereto, and the mixture was stirred for 10 minutes. The reaction mixture was stirred for additional 30 minutes at room temperature, and ice cooled, and then 10 ml of water, 10 ml of aqueous 15% sodium hydroxide and 30 ml of water were added thereto in order. The mixture was filtered by use of a filter aid and then concentrated under reduced pressure to afford 53.54 g of the desired compound as an oily matter.

NMR (CDCl$_3$) δ (ppm): 7.45–6.85, 5.77, 5.12, 4.60, 4.47

Reference Example 6

2-[Bis(4-benzyloxyphenyl)methyl]benzyl alcohol

The desired compound (69.03 g) was obtained from 114.61 g of benzyl 2-[bis(4-benzyloxyphenyl)methyl]benzoate obtained by Reference Example 4 in a similar manner as in Reference Example 5.

NMR (CDCl$_3$) δ (ppm): 7.40–7.10, 7.00–6.75, 5.73, 4.98, 4.61

Reference Example 7

2-[Bis(4-methoxymethoxyphenyl)methyl]benzaldehyde

In 400 ml of dichloromethane was dissolved 58.3 g of 2-[bis(4-methoxymethoxyphenyl)methyl]benzyl alcohol obtained by Reference Example 5, and the solution was ice cooled.

Subsequently, 110 g of pyridinium dichromate was added to the solution, and the mixture was stirred for 15 minutes. The mixture was then additionally stirred for one day at room temperature. To the reaction mixture was added 77 ml of isopropyl alcohol, and the mixture was stirred for 20 minutes. The mixture was diluted with ethyl acetate, filtered by using a filter aid and then concentrated under reduced pressure to afford 50.77 g of the desired compound as an oily matter.

NMR (CDCl$_3$) δ (ppm): 10.18, 8.51, 8.85–8.75, 8.38–6.92, 6.43, 5.10, 3.43

Reference Example 8

2-[Bis(4-benzyloxyphenyl)methyl]benzaldehyde

The desired compound (50.58 g) was obtained from 69 g of 2-[bis(4-benzyloxyphenyl)methyl]benzyl alcohol obtained by Reference Example 6 in a similar manner as in Reference Example 7.

NMR (CDCl$_3$) δ (ppm): 10.19, 9.98, 8.56, 7.9–7.78, 7.60–7 15, 7.00–6.78, 6.42, 4.99

Reference Example 9

N-[2-Bis(4-benzyloxyphenyl)methylbenzylidene]-(1-benzylpiperidin-4-yl)amine

In a mixture of 20 ml of ethanol and 20 ml of dioxane were dissolved 5 g of 2-[bis(4-benzyloxyphenyl)methyl]benzaldehyde obtained by Reference Example 8 and 2.1 ml of 4-amino-1-benzylpiperidine, and the solution was heated under reflux for 4.5 hours. The solvent was then evaporated under reduced pressure to afford 7.0 g of the desired compound.

NMR (CDCl$_3$) δ (ppm): 8.46, 7.77, 7.50–7.00, 6.86, 6.00, 4.98, 3.48, 3.20–2.70, 2.30–1.40

Reference Example 10

4,4'-Diacetoxy-2''-nitrotriphenylmethane

In 80 ml of pyridine was dissolved 12 g of 4,4'-dihydroxy-2''-nitrotriphenylmethane, and then 40 ml of acetic anhydride was added dropwise to the solution. The mixture was stirred for one day, and washed with 2N hydrochloric acid and then extracted with ethyl acetate. The extract was dried over anhydrous magnesium sulfate and then subjected to crystallization from a mixture of ether and hexane to afford 9.46 g of the desired compound.

NMR (CDCl$_3$) δ (ppm): 7.93–7.82, 7.52–7.04, 6.27, 2.31

Reference Example 11

4,4'-Diacetoxy-2''-aminotriphenylmethane

In a mixture of 180 ml of dioxane and 20 ml of ethanol was dissolved 7.68 g of 4,4'-diacetoxy-2''-nitrotriphenylmethane obtained by Reference Example 10. Thereafter, a mixture of 98 mg of 10% palladium-carbon and 10 ml of water was added thereto, and the mixture was stirred at room temperature for 8 hours, while being contacted with hydrogen. The reaction mixture was filtered by using a filter aid, and the filtrate was then concentrated to give 7.71 g of the desired compound.

NMR (CDCl$_3$) δ (ppm): 7.40-6.80, 6.75-6.6 3.10-2.50, 2.25

Reference Example 12

4,4'-Bis(methoxymethoxy)-2"-nitrotriphenylmethane

In 500 ml of methylene chloride was dissolved 93 g of 4,4'-dihydroxy-2"-nitrotriphenylmethane. To this solution were added 135 g of N,N-diisopropylethylamine and 77 ml of chloromethyl methyl ether, and the mixture was stirred at room temperature for 5.5 hours. Thereafter, the solvent was evaporated under reduced pressure, and the residue was subjected to extraction with water and ethyl acetate. The organic layer was separated, and the aqueous layer was extracted with ethyl acetate. The organic layers were combined, washed with saturated aqueous sodium chloride, and then purified by silica gel column chromatography to afford 19.5 g of the desired compound as an oily matter.

NMR (CDCl$_3$) δ (ppm): 7.80, 7.45-6.75, 6.13, 5.10, 3.45

Reference Example 13

4,4'-Bis(methoxymethoxy)-2"-aminotriphenylmethane

In a mixture of 40 ml of ethanol and 350 ml of dioxane was dissolved 19.5 g of 4,4'-bis(methoxymethoxy)-2"-nitrotriphenylmethane obtained by Reference Example 12. In the solution was suspended 0.25 g of 10% palladium-carbon, and the suspension was stirred under hydrogen atmosphere for 2 days. The reaction mixture was filtered by the using a filter aid. The solvent was then evaporated to afford 20.1 g of the desired compound.

NMR (CDCl$_3$) δ (ppm): 7.20-6.40, 5.30, 5.06, 3.40

What is claimed is:

1. A triphenylmethane derivative represented by the following formula:

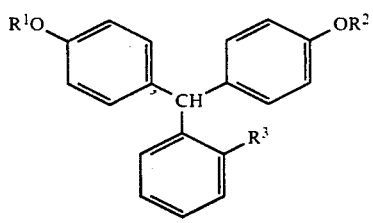

wherein R$^1$ and R$^2$ are independently hydrogen, C1-6 alkyl, benzyl, C1-5 alkanoyl or C1-6 alkoxymethyl; R$^3$ is —CONR$^4$R$^5$ {wherein R$^4$ is C3-8 cycloalkyl, allyl, styryl, optionally substituted phenethyl, optionally substituted 1,2-diphenylethyl, optionally substituted benzhydryl, optionally substituted trityl and optionally substituted benzyl, (which may be optionally mono-, di- or tri-substituted by C1-6 alkyl, trifluoromethyl, hydroxyl, C1-6 alkoxy, C1-6 alkylthio, halogen, nitro, amino, C1-5 alkanoyl, aroyl, morpholino, carboxyl or C1-6 alkoxycarbonyl in the aryl moiety), substituted phenyl or substituted naphthyl (which may be mono-, di- or tri-substituted by C1-6 alkyl, trifluoromethyl, C1-6 alkoxy, C1-6 alkylthio, halogen, nitro, C1-5 alkanoyl, aroyl or C1-6 alkoxycarbonyl),

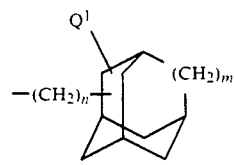

(wherein Q1 is hydrogen or C1-6 alkyl, m is 0 or 1, and n is an integer of 0 to 5),

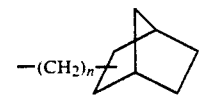

(wherein n is an integer of 0 to 5),

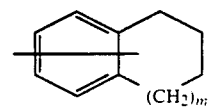

(wherein m is 0 or 1), and

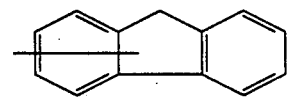

and R$^5$ is hydrogen, optionally substituted C1-6 alkyl (which may be mono, di- or tri-substituted by C1-6 alkoxy, mono- or di- C1-6 alkyl-substituted amino or halogen, C3-8 cycloalkyl, allyl, styryl), optionally substituted phenethyl, optionally substituted 1,2-diphenylethyl, optionally substituted benzhydryl, optionally substituted trityl or optionally substituted benzyl, (which may be mono, do- or tri-substituted by C1-6 alkyl, trifluoromethyl, hydroxyl, C1-6 alkoxy, C1-6 aklylthio, halogen, nitro, amino, C1-5 alkanoyl, aroyl, morpholino, carboxyl or C1-6 alkoxycarbonyl in the aryl moiety), optionally substituted phenyl or optionally substituted naphthyl, (which may be mono, di- or tri-substituted by C1-6 aklylthio, halogen, nitro, amino, C1-5 alkanoyl, aroyl, morpholino, carboxyl or C1-6 alkoxycarbonyl)

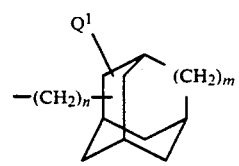

(wherein A$^1$ is selected from hydrogen and C1-6 alkyl, m is 0 or 1, and n is an integer of 0 to 5),

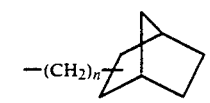

(wherein n is an integer of 0 to 5),

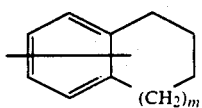

(wherein m is 0 or 1), and

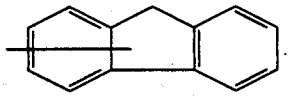

2. A compound according claim 1, wherein $R^1$ and $R^2$ represent hydrogen.

3. A compound according claim 2, wherein $R^5$ is H.

4. A compound according claim 3, wherein $R^4$ represents C6-8 cycloalkyl.

5. N-Cyclooctyl-2-[bis(4-hydroxyphenyl) methyl]-benzamide.

6. A compound according claim 3, wherein $R^4$ represents

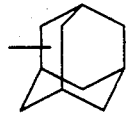

7. N-(Tricyclo[3.3.1$^{13,7}$]dec-2-yl)-2-[bis(4-hydroxyphenyl)methyl]benzamide.

8. A pharmaceutical composition comprising a pharmaceutical carrier and, as an active ingredient, an effective amount of the compound as defined by claim 1.

* * * * *

UNITED STATES PATENT AND TRADEMARK OFFICE
CERTIFICATE OF CORRECTION

PATENT NO. : 5,112,867
DATED     : May 12, 1992
INVENTOR(S) : IWAO KINOSHITA ET AL.

It is certified that error appears in the above-identified patent and that said Letters Patent is hereby corrected as shown below:

ON THE TITLE PAGE,
AT [73] ASSIGNEE

"Gogyo" should read --Kogyo--

ON THE TITLE PAGE,
AT [56] REFERENCES CITED

Other Publications,
  "113:90516v." should read --113:190516v.--.

ON THE TITLE PAGE,
AT [57] ABSTRACT

"born" should read --bone--.

COLUMN 1

Line 19, "(1952)" should read --(1959)--.

COLUMN 4

Line 20, "  " should read --  --.

Line 55, "other groups" should read --groups other--.
Line 65, "other groups" should read --groups other--.
Line 66, "other groups" should read --groups other--.
Line 68, "other groups" should read --groups other--.

UNITED STATES PATENT AND TRADEMARK OFFICE
CERTIFICATE OF CORRECTION

PATENT NO. : 5,112,867
DATED : May 12, 1992
INVENTOR(S) : IWAO KINOSHITA ET AL.

It is certified that error appears in the above-identified patent and that said Letters Patent is hereby corrected as shown below:

COLUMN 6

Line 26, "other groups" should read --groups other--.

COLUMN 7

Line 15, "other groups" should read --groups other--.
Line 16, "other groups" should read --groups other--.
Line 17, "other groups" should read --groups other--.
Line 19, "other groups" should read --groups other--.

COLUMN 8

Line 65, "other groups" should read --groups other-- and "$R^{61}$" should read --$R^{6a}$--.

COLUMN 39

Table 1, "$CH_3OCH_2$" (both occurrences) should read --$CH_3COCH_2$--.
Line 31, "(1x10-4M)" should read --($1x10^{-4}$M)--.

COLUMN 45

Line 7, "377," should read --1377,--.
Line 18, "479," should read --1479,--.
Line 20, "5" should be deleted.
Line 29, "379," should read --1379,-- and "823," should read --823,744--.
Line 39, "477," should read --1477,--.

UNITED STATES PATENT AND TRADEMARK OFFICE
CERTIFICATE OF CORRECTION

PATENT NO. : 5,112,867
DATED : May 12, 1992
INVENTOR(S) : IWAO KINOSHITA ET AL.

It is certified that error appears in the above-identified patent and that said Letters Patent is hereby corrected as shown below:

<u>COLUMN 61</u>

Line 7, "280-182°C" should read --280-282°C--.

<u>COLUMN 65</u>

Line 55, "{wherein" should read --, wherein--.

<u>COLUMN 66</u>

Line 43, "aklylthio," should read --alkylthio,--.
Line 46, "naphthyl," should read --naphthyl--.
Line 47, "aklylthio," should read --alkylthio,--.
Line 59, "$A^1$" should read --$Q^1$--.

Signed and Sealed this

Eighth Day of December, 1992

Attest:

DOUGLAS B. COMER

Attesting Officer    Acting Commissioner of Patents and Trademarks